(12) United States Patent
Levi et al.

(10) Patent No.: US 11,103,345 B2
(45) Date of Patent: *Aug. 31, 2021

(54) PROSTHETIC HEART VALVE

(71) Applicant: Edwards Lifesciences Corporation, Irvine, CA (US)

(72) Inventors: Tamir S. Levi, Zikhron Yaakov (IL); Ron Sharoni, Hadera (IL); Elena Sherman, Pardes Hanna (IL); Oren H. Wintner, Jerusalem (IL); Kevin D. Rupp, Irvine, CA (US); Son V. Nguyen, Irvine, CA (US); Ajay Chadha, Irvine, CA (US); Jeff Lindstrom, Coto de Caza, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 67 days.

This patent is subject to a terminal disclaimer.

(21) Appl. No.: 16/262,188

(22) Filed: Jan. 30, 2019

(65) Prior Publication Data

US 2019/0159895 A1 May 30, 2019

Related U.S. Application Data

(63) Continuation of application No. 14/704,861, filed on May 5, 2015, now Pat. No. 10,195,025.

(Continued)

(51) Int. Cl.
*A61F 2/24* (2006.01)
*A61F 2/95* (2013.01)

(52) U.S. Cl.
CPC .......... *A61F 2/2418* (2013.01); *A61F 2/2412* (2013.01); *A61F 2/2427* (2013.01);
(Continued)

(58) Field of Classification Search
CPC .... A61F 2/2418; A61F 2/2427; A61F 2/9522; A61F 2220/0025; A61F 2220/0075;
(Continued)

(56) References Cited

U.S. PATENT DOCUMENTS 3,365,728 A   1/1968 Edwards et al.
3,725,961 A   4/1973 Magovern et al.
(Continued)

FOREIGN PATENT DOCUMENTS

AU   2002212418 B2   3/2006
AU   2011253834 A1   1/2012
(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.
(Continued)

*Primary Examiner* — Jocelin C Tanner
(74) *Attorney, Agent, or Firm* — Klarquist Sparkman, LLP; Joel B. German

(57) ABSTRACT

Embodiments of a radially collapsible and expandable prosthetic heart valve are disclosed. The prosthetic valve can comprise an annular frame, leaflets, an inner skirt, and an outer skirt. The outer skirt can be secured to the outside of the inflow end portion of the frame, the outer skirt having longitudinal slack that buckles outward radially when the valve is in the expanded configuration and which lies flat when the valve is in the collapsed configuration. In some embodiments, the outer skirt is stiffer in the axial direction of the valve than in the circumferential direction of the valve. In additional embodiments, the outer skirt comprises a self-expandable fabric comprising fibers made of a shape
(Continued)

memory material having a shape memory set to enhance the radially outward buckling of the outer skirt. Methods of crimping such valves to a collapsed or partially collapsed configuration are also disclosed.

19 Claims, 23 Drawing Sheets

Related U.S. Application Data

(60) Provisional application No. 61/991,904, filed on May 12, 2014.

(52) U.S. Cl.
CPC ..... *A61F 2/9522* (2020.05); *A61F 2220/0025* (2013.01); *A61F 2220/0075* (2013.01); *A61F 2230/0019* (2013.01); *A61F 2230/0054* (2013.01); *A61F 2250/0018* (2013.01); *A61F 2250/0039* (2013.01); *A61F 2250/0069* (2013.01); *Y10T 29/49927* (2015.01)

(58) Field of Classification Search
CPC ...... A61F 2230/0019; A61F 2230/0054; A61F 2250/0018; A61F 2250/0036; A61F 2250/0069; Y10T 29/49927
See application file for complete search history.

(56) References Cited

U.S. PATENT DOCUMENTS

| | | |
|---|---|---|
| 3,755,823 A | 9/1973 | Hancock |
| 3,983,581 A | 10/1976 | Angell et al. |
| 4,035,849 A | 7/1977 | Angell et al. |
| 4,610,688 A | 9/1986 | Silvestrini et al. |
| 4,777,951 A | 10/1988 | Cribier et al. |
| 4,787,899 A | 11/1988 | Lazarus |
| 4,796,629 A | 1/1989 | Grayzel |
| 4,856,516 A | 8/1989 | Hillstead |
| 4,878,495 A | 11/1989 | Grayzel |
| 4,966,604 A | 10/1990 | Reiss |
| 4,994,077 A | 2/1991 | Dobben |
| 5,059,177 A | 10/1991 | Towne et al. |
| 5,178,630 A * | 1/1993 | Schmitt ............... A61F 2/06 623/1.33 |
| 5,192,297 A | 3/1993 | Hull |
| 5,258,023 A | 11/1993 | Reger |
| 5,282,847 A | 2/1994 | Trescony et al. |
| 5,370,685 A | 12/1994 | Stevens |
| 5,411,552 A | 5/1995 | Andersen et al. |
| 5,476,506 A | 12/1995 | Lunn |
| 5,509,931 A | 4/1996 | Schmitt |
| 5,545,214 A | 8/1996 | Stevens |
| 5,554,185 A | 9/1996 | Block et al. |
| 5,558,644 A | 9/1996 | Boyd et al. |
| 5,584,803 A | 12/1996 | Stevens et al. |
| 5,591,195 A | 1/1997 | Taheri et al. |
| 5,606,928 A | 3/1997 | Religa et al. |
| 5,607,464 A | 3/1997 | Trescony et al. |
| 5,628,786 A | 5/1997 | Banas et al. |
| 5,665,115 A | 9/1997 | Cragg |
| 5,693,088 A | 12/1997 | Lazarus |
| 5,755,783 A | 5/1998 | Stobie et al. |
| 5,769,812 A | 6/1998 | Stevens et al. |
| 5,769,882 A | 6/1998 | Fogarty et al. |
| 5,776,188 A | 7/1998 | Shepherd et al. |
| 5,800,508 A | 9/1998 | Goicoechea et al. |
| 5,840,081 A | 11/1998 | Andersen et al. |
| 5,843,161 A | 12/1998 | Solovay |
| 5,843,179 A | 12/1998 | Vanney et al. |
| 5,855,597 A | 1/1999 | Jayaraman |
| 5,855,601 A | 1/1999 | Bessler et al. |
| 5,925,063 A | 7/1999 | Khosravi |
| 5,957,949 A | 9/1999 | Leonhardt et al. |
| 5,976,179 A | 11/1999 | Inoue |
| 6,015,431 A | 1/2000 | Thornton et al. |
| 6,027,525 A | 2/2000 | Suh et al. |
| 6,110,198 A | 8/2000 | Fogarty et al. |
| 6,168,614 B1 | 1/2001 | Andersen et al. |
| 6,206,911 B1 | 3/2001 | Milo |
| 6,221,091 B1 | 4/2001 | Khosravi |
| 6,245,102 B1 | 6/2001 | Jayaraman |
| 6,302,906 B1 | 10/2001 | Goecoechea et al. |
| 6,306,164 B1 | 10/2001 | Kujawski |
| 6,352,554 B2 | 3/2002 | De Paulis |
| 6,425,916 B1 | 7/2002 | Garrison et al. |
| 6,454,799 B1 | 9/2002 | Schreck |
| 6,458,153 B1 | 10/2002 | Bailey et al. |
| 6,461,382 B1 | 10/2002 | Cao |
| 6,482,228 B1 | 11/2002 | Norred |
| 6,527,979 B2 | 3/2003 | Constantz |
| 6,540,782 B1 | 4/2003 | Snyders |
| 6,582,462 B1 | 6/2003 | Andersen et al. |
| 6,652,578 B2 | 11/2003 | Bailey et al. |
| 6,663,667 B2 | 12/2003 | Dehdashtian et al. |
| 6,729,356 B1 | 5/2004 | Baker et al. |
| 6,730,118 B2 | 5/2004 | Spenser et al. |
| 6,733,525 B2 | 5/2004 | Yang et al. |
| 6,767,362 B2 | 7/2004 | Schreck |
| 6,773,456 B1 | 8/2004 | Gordon et al. |
| 6,814,754 B2 | 11/2004 | Greenhalgh |
| 6,830,584 B1 | 12/2004 | Seguin |
| 6,846,325 B2 | 1/2005 | Liddicoat |
| 6,878,162 B2 | 4/2005 | Bales et al. |
| 6,893,460 B2 | 5/2005 | Spenser et al. |
| 6,904,909 B2 | 6/2005 | Andreas et al. |
| 6,908,481 B2 | 6/2005 | Cribier |
| 6,911,040 B2 | 6/2005 | Johnson et al. |
| 7,018,406 B2 | 3/2006 | Seguin et al. |
| 7,018,408 B2 | 3/2006 | Bailey et al. |
| 7,101,396 B2 | 9/2006 | Artof et al. |
| 7,147,663 B1 | 12/2006 | Berg et al. |
| 7,175,652 B2 | 2/2007 | Cook et al. |
| 7,192,441 B2 | 3/2007 | Sherry |
| 7,264,632 B2 | 9/2007 | Wright et al. |
| 7,276,078 B2 | 10/2007 | Spenser et al. |
| 7,276,084 B2 | 10/2007 | Yang et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |
| 7,530,253 B2 | 5/2009 | Spenser et al. |
| 7,585,321 B2 | 9/2009 | Cribier |
| 7,618,446 B2 | 11/2009 | Andersen et al. |
| 7,655,034 B2 | 2/2010 | Mitchell et al. |
| 7,731,742 B2 | 6/2010 | Schlick et al. |
| 7,780,725 B2 | 8/2010 | Haug et al. |
| 7,785,366 B2 | 8/2010 | Maurer et al. |
| 7,895,876 B2 | 3/2011 | Spenser et al. |
| 7,959,672 B2 | 6/2011 | Salahieh et al. |
| 7,993,394 B2 | 8/2011 | Hariton et al. |
| 8,029,556 B2 | 10/2011 | Rowe |
| 8,105,377 B2 | 1/2012 | Liddicoat |
| 8,128,681 B2 | 3/2012 | Shoemaker et al. |
| 8,167,932 B2 | 5/2012 | Bourang |
| 8,177,834 B2 | 5/2012 | Carlson et al. |
| 8,425,593 B2 | 4/2013 | Braido et al. |
| 8,430,925 B2 | 4/2013 | Forster et al. |
| 8,449,606 B2 | 5/2013 | Eliasen et al. |
| 8,721,717 B2 | 5/2014 | Shoemaker et al. |
| 8,795,357 B2 | 8/2014 | Yohanan et al. |
| 8,808,356 B2 | 8/2014 | Braido et al. |
| 8,845,721 B2 | 9/2014 | Braido et al. |
| 8,979,922 B2 | 3/2015 | Jayasinghe et al. |
| 8,992,608 B2 | 3/2015 | Haug et al. |
| 9,220,594 B2 | 12/2015 | Braido et al. |
| 9,241,794 B2 | 1/2016 | Braido et al. |
| 9,289,296 B2 | 3/2016 | Braido et al. |
| 9,326,856 B2 | 5/2016 | Schraut et al. |
| 9,345,571 B1 | 5/2016 | Braido et al. |
| 9,351,828 B2 | 5/2016 | Braido et al. |
| 9,351,831 B2 | 5/2016 | Braido et al. |

(56) References Cited

U.S. PATENT DOCUMENTS

| | | | |
|---|---|---|---|
| 9,351,832 B2 | 5/2016 | Braido et al. |
| 9,414,911 B2 | 8/2016 | Braido et al. |
| 9,545,307 B2 | 1/2017 | Braido et al. |
| 9,549,815 B2 | 1/2017 | Braido et al. |
| 10,195,025 B2* | 2/2019 | Levi | A61F 2/2412 |
| 2001/0021872 A1 | 9/2001 | Bailey et al. |
| 2001/0027338 A1 | 10/2001 | Greenberg |
| 2001/0039450 A1 | 11/2001 | Pavcnik et al. |
| 2002/0026094 A1 | 2/2002 | Roth |
| 2002/0032481 A1 | 3/2002 | Gabbay |
| 2002/0138135 A1 | 9/2002 | Duerig et al. |
| 2003/0050694 A1 | 3/2003 | Yang et al. |
| 2003/0074058 A1 | 4/2003 | Sherry |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2003/0236567 A1 | 12/2003 | Elliot |
| 2004/0033364 A1 | 2/2004 | Spiridigliozzi et al. |
| 2004/0082989 A1 | 4/2004 | Cook et al. |
| 2004/0098096 A1 | 5/2004 | Eton |
| 2004/0186563 A1 | 9/2004 | Lobbi |
| 2004/0186565 A1 | 9/2004 | Schreck |
| 2004/0210304 A1 | 10/2004 | Seguin et al. |
| 2004/0260389 A1 | 12/2004 | Case et al. |
| 2005/0043790 A1 | 2/2005 | Seguin |
| 2005/0096736 A1 | 5/2005 | Osse et al. |
| 2005/0137687 A1 | 6/2005 | Salahieh et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2006/0025857 A1 | 2/2006 | Bergheim et al. |
| 2006/0058872 A1 | 3/2006 | Salahieh et al. |
| 2006/0149350 A1 | 7/2006 | Patel et al. |
| 2007/0005131 A1 | 1/2007 | Taylor |
| 2007/0010877 A1 | 1/2007 | Salahieh et al. |
| 2007/0061009 A1 | 3/2007 | Spenser et al. |
| 2007/0073387 A1 | 3/2007 | Forster et al. |
| 2007/0112422 A1 | 5/2007 | Dehdashtian |
| 2007/0203503 A1 | 8/2007 | Salahieh et al. |
| 2007/0203575 A1 | 8/2007 | Forster et al. |
| 2007/0265700 A1 | 11/2007 | Eliasen et al. |
| 2008/0114442 A1 | 5/2008 | Mitchell et al. |
| 2008/0125853 A1 | 5/2008 | Bailey et al. |
| 2008/0228028 A1 | 9/2008 | Carlson et al. |
| 2008/0262595 A1* | 10/2008 | Chu | A61F 2/962 |
| | | | 623/1.13 |
| 2009/0099653 A1 | 4/2009 | Suri et al. |
| 2009/0132035 A1 | 5/2009 | Roth et al. |
| 2009/0157175 A1 | 6/2009 | Benichou |
| 2009/0264997 A1 | 10/2009 | Salahieh et al. |
| 2009/0276040 A1 | 11/2009 | Rowe et al. |
| 2009/0281619 A1 | 11/2009 | Le et al. |
| 2009/0319037 A1 | 12/2009 | Rowe et al. |
| 2009/0319038 A1* | 12/2009 | Gurskis | A61F 2/2418 |
| | | | 623/2.36 |
| 2010/0043197 A1 | 2/2010 | Abbate et al. |
| 2010/0049313 A1 | 2/2010 | Alon et al. |
| 2010/0168839 A1 | 7/2010 | Braido et al. |
| 2010/0198347 A1 | 8/2010 | Zakay et al. |
| 2011/0015729 A1 | 1/2011 | Jimenez et al. |
| 2011/0264205 A1 | 10/2011 | Righini et al. |
| 2012/0035719 A1 | 2/2012 | Forster et al. |
| 2012/0101569 A1 | 4/2012 | Mearns et al. |
| 2012/0116492 A1* | 5/2012 | Seibold | A61L 31/10 |
| | | | 623/1.11 |
| 2012/0123529 A1* | 5/2012 | Levi | A61F 2/2412 |
| | | | 623/2.11 |
| 2012/0215303 A1 | 8/2012 | Quadri et al. |
| 2012/0271398 A1 | 10/2012 | Essinger et al. |
| 2013/0023985 A1 | 1/2013 | Khairkhahan et al. |
| 2013/0274873 A1 | 10/2013 | Delaloye et al. |
| 2013/0317598 A1 | 11/2013 | Rowe et al. |
| 2013/0338765 A1 | 12/2013 | Braido et al. |
| 2014/0350663 A1 | 11/2014 | Braido et al. |
| 2015/0073541 A1 | 3/2015 | Salahieh et al. |
| 2015/0073546 A1 | 3/2015 | Braido |
| 2015/0157455 A1 | 6/2015 | Hoang et al. |
| 2015/0282932 A1 | 10/2015 | Neuman et al. |
| 2016/0213466 A1 | 7/2016 | Braido et al. |
| 2016/0213468 A1 | 7/2016 | Braido et al. |
| 2016/0242904 A1 | 8/2016 | Braido et al. |

FOREIGN PATENT DOCUMENTS

| | | |
|---|---|---|
| CN | 1961845 A | 5/2007 |
| CN | 1961847 A | 5/2007 |
| CN | 102970944 A | 3/2013 |
| CN | 103237524 A | 8/2013 |
| CN | 103517689 A | 1/2014 |
| CN | 103687574 A | 3/2014 |
| DE | 19532846 A1 | 3/1997 |
| DE | 19546692 A1 | 6/1997 |
| DE | 19857887 A1 | 7/2000 |
| DE | 19907646 A1 | 8/2000 |
| EP | 0103546 A1 | 3/1984 |
| EP | 0597967 A1 | 5/1994 |
| EP | 0592410 B1 | 10/1995 |
| EP | 0850607 A1 | 7/1998 |
| EP | 1346705 A1 | 9/2003 |
| EP | 1796597 A2 | 6/2007 |
| EP | 2155114 A1 | 2/2010 |
| EP | 2299938 A2 | 3/2011 |
| EP | 2471490 A2 | 7/2012 |
| EP | 2572676 A3 | 8/2013 |
| EP | 2572675 A3 | 9/2013 |
| EP | 2698129 A1 | 2/2014 |
| EP | 2815725 A1 | 12/2014 |
| EP | 2745805 B1 | 6/2015 |
| EP | 2749254 B1 | 6/2015 |
| EP | 2967851 A2 | 1/2016 |
| EP | 2926766 B1 | 2/2016 |
| EP | 2815725 B1 | 4/2016 |
| EP | 2815724 B1 | 6/2016 |
| EP | 3028670 A1 | 6/2016 |
| EP | 3028671 A1 | 6/2016 |
| EP | 2815723 B1 | 7/2016 |
| EP | 3025680 B1 | 2/2017 |
| EP | 3025681 B1 | 2/2017 |
| EP | 2190385 B1 | 3/2017 |
| FR | 2788217 A1 | 7/2000 |
| FR | 2815844 A1 | 5/2002 |
| JP | 2005185529 A | 7/2005 |
| JP | 2011522634 A | 8/2011 |
| SU | 1271508 A1 | 11/1986 |
| WO | 9117720 A1 | 11/1991 |
| WO | 9301768 A1 | 2/1993 |
| WO | 9829057 A1 | 7/1998 |
| WO | 9904730 A1 | 2/1999 |
| WO | 9748350 A8 | 6/1999 |
| WO | 9940964 A1 | 8/1999 |
| WO | 9947075 A1 | 9/1999 |
| WO | 2000041652 A1 | 7/2000 |
| WO | 0044313 A1 | 8/2000 |
| WO | 0106959 A1 | 2/2001 |
| WO | 0149213 A2 | 7/2001 |
| WO | 0154625 A1 | 8/2001 |
| WO | 0162189 A1 | 8/2001 |
| WO | 0047139 A9 | 9/2001 |
| WO | 0164137 A1 | 9/2001 |
| WO | 0176510 A2 | 10/2001 |
| WO | 0219951 A1 | 3/2002 |
| WO | 0222054 A1 | 3/2002 |
| WO | 0236048 A1 | 5/2002 |
| WO | 0247575 A2 | 6/2002 |
| WO | 03003949 A2 | 1/2003 |
| WO | 03047468 A1 | 6/2003 |
| WO | 03037222 A3 | 10/2003 |
| WO | 03088873 A1 | 10/2003 |
| WO | 03096932 A1 | 11/2003 |
| WO | 2005034812 A1 | 4/2005 |
| WO | 2005084595 A1 | 9/2005 |
| WO | 2006111391 A1 | 10/2006 |
| WO | 2006126182 A2 | 11/2006 |
| WO | 2006138173 A2 | 12/2006 |

(56) References Cited

FOREIGN PATENT DOCUMENTS

| WO | 2005102015 A3 | 4/2007 |
|----|---------------|--------|
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008091515 A2 | 7/2008 |
| WO | 2009033469 A1 | 3/2009 |
| WO | 2009038761 A1 | 3/2009 |
| WO | 2010008548 A2 | 1/2010 |
| WO | 2010111666 A1 | 9/2010 |
| WO | 2010121076 A2 | 10/2010 |
| WO | 2012048035 A2 | 4/2012 |
| WO | 2013033791 A1 | 3/2013 |
| WO | 2013177684 A1 | 12/2013 |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

International Search Report from corresponding PCT case No. PCT/US2015/029614 dated Jul. 24, 2015.

Office Action for corresponding case CN appl. 2015800010576 dated Aug. 23, 2016.

Office Action dated Oct. 30, 2018, Application No. 15783951.5.

\* cited by examiner

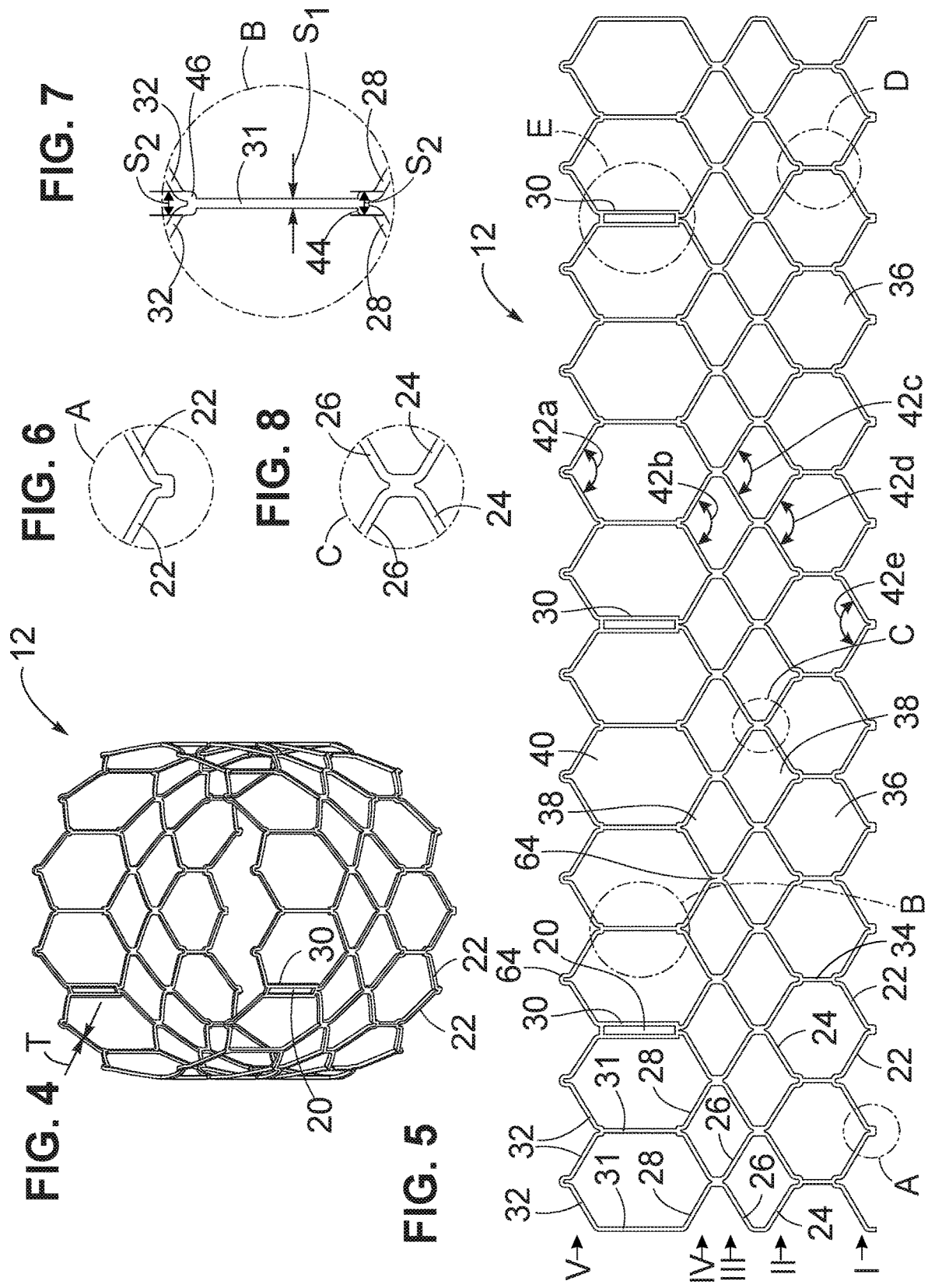

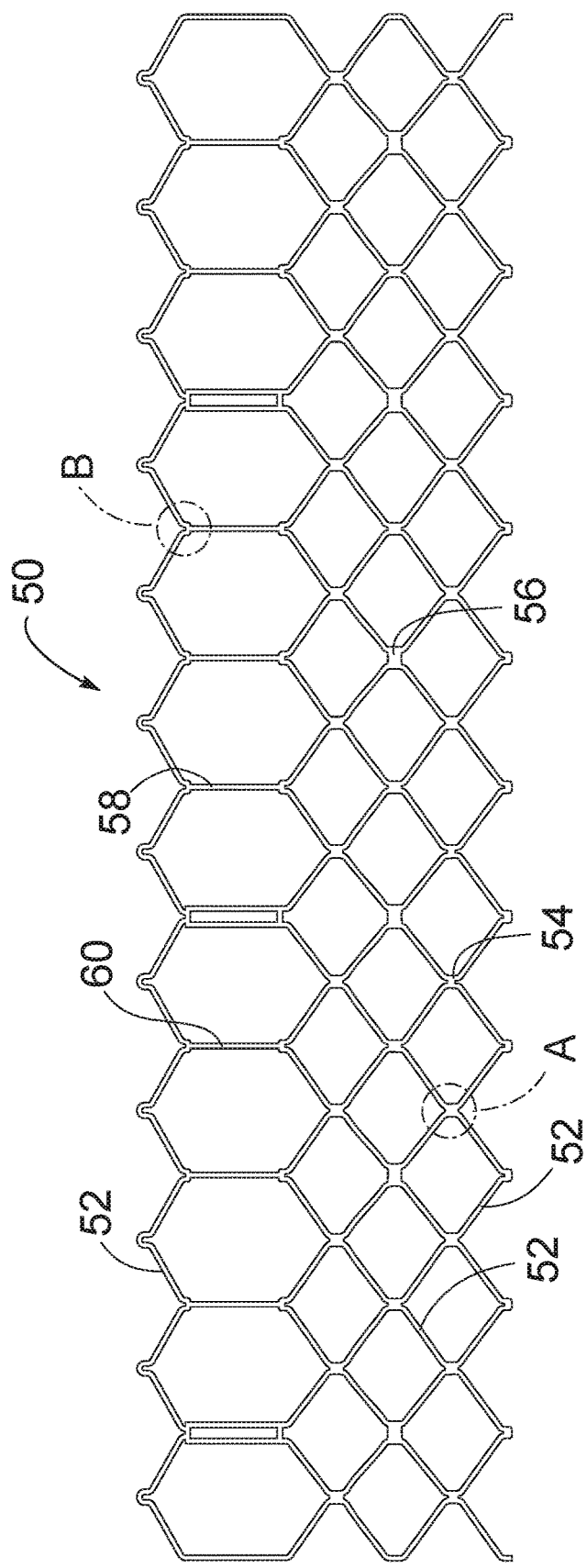
FIG. 12
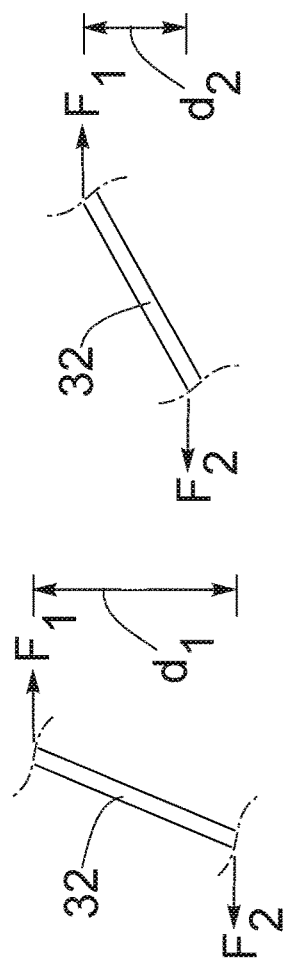
FIG. 15A
FIG. 15B
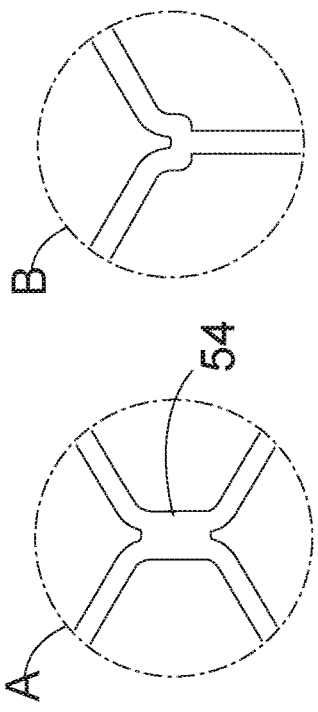
FIG. 13
FIG. 14

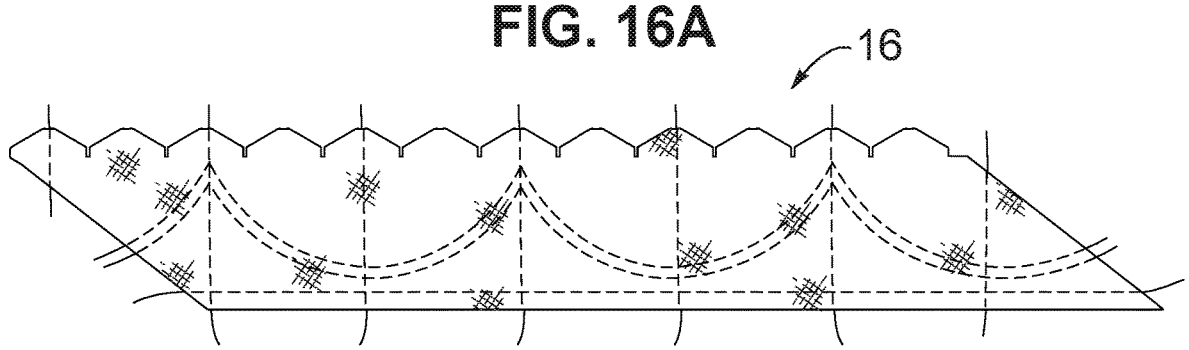
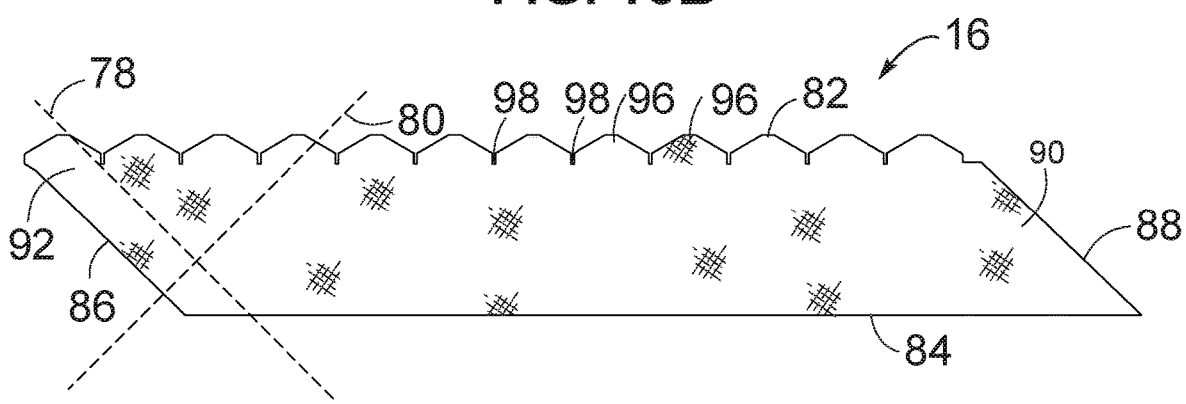
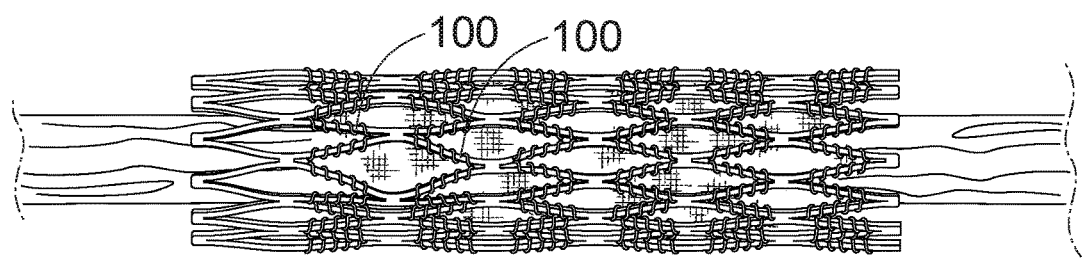
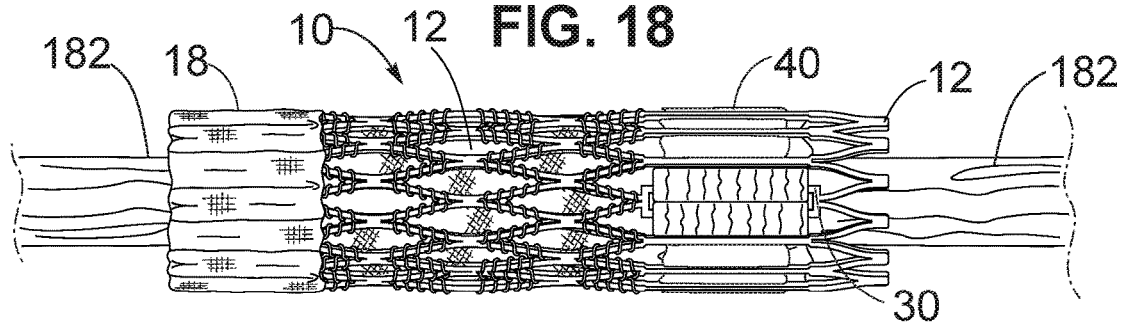

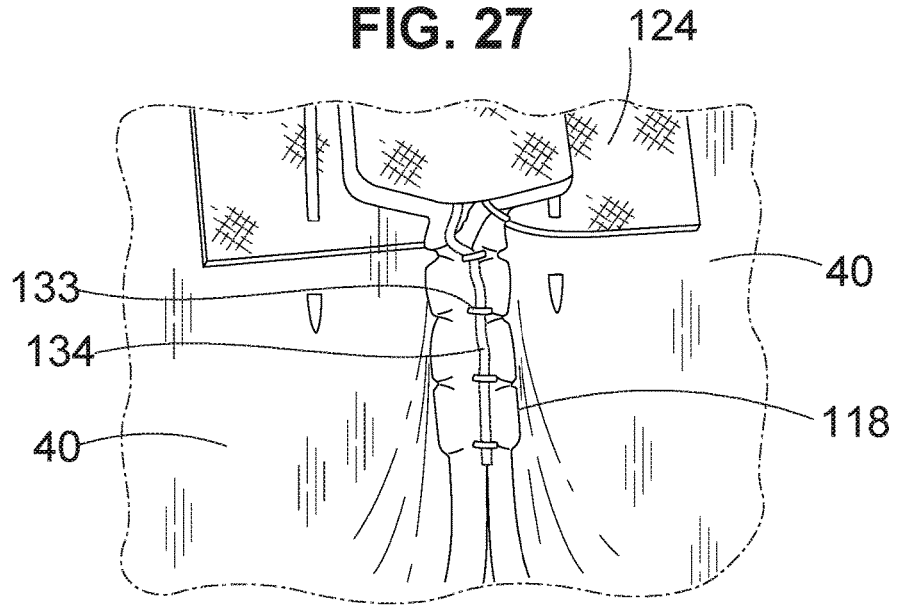
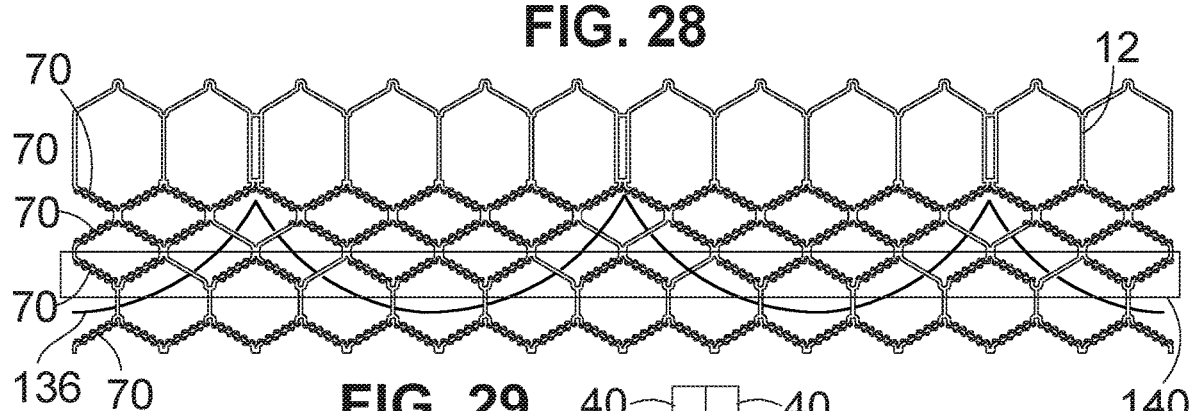
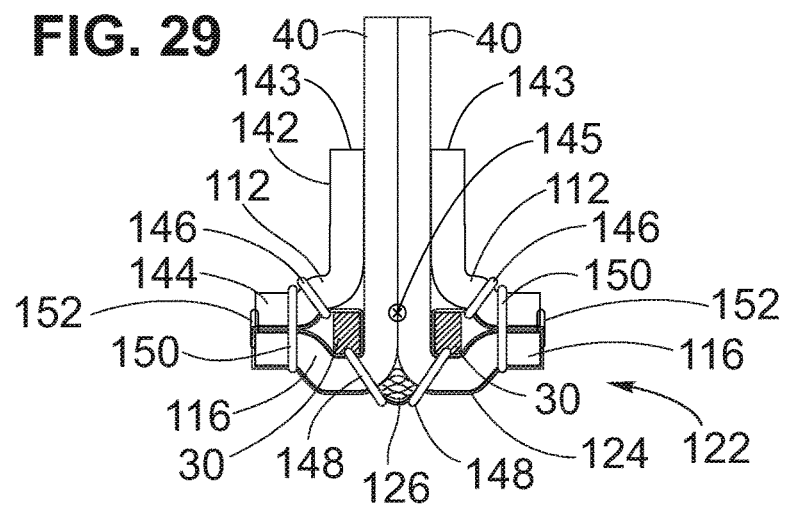

PROSTHETIC HEART VALVE

CROSS REFERENCE TO RELATED APPLICATIONS

This application is a continuation of U.S. patent application Ser. No. 14/704,861, filed May 5, 2015, which in turn claims the benefit of U.S. Provisional Application No. 61/991,904, filed May 12, 2014, each of which is incorporated by reference herein in its entirety.

FIELD

The present disclosure relates to implantable expandable prosthetic devices and to methods for crimping a prosthetic device.

BACKGROUND

The human heart can suffer from various valvular diseases. These valvular diseases can result in significant malfunctioning of the heart and ultimately require replacement of the native valve with an artificial valve. There are a number of known artificial valves and a number of known methods of implanting these artificial valves in humans. Because of the drawbacks associated with conventional open-heart surgery, percutaneous and minimally-invasive surgical approaches are garnering intense attention. In one technique, a prosthetic valve is configured to be implanted in a much less invasive procedure by way of catheterization. For example, collapsible transcatheter prosthetic heart valves can be crimped to a compressed state and percutaneously introduced in the compressed state on a catheter and expanded to a functional size at the desired position by balloon inflation or by utilization of a self-expanding frame or stent.

A prosthetic valve for use in such a procedure can include a radially collapsible and expandable frame to which leaflets of the prosthetic valve can be coupled. For example, U.S. Pat. Nos. 6,730,118, 7,393,360, 7,510,575, and 7,993,394, which are incorporated herein by reference, describe exemplary collapsible transcatheter prosthetic heart valves.

A prosthetic valve for use in such a procedure can include a radially collapsible and expandable frame to which leaflets of the prosthetic valve can be coupled, and which can be percutaneously introduced in a collapsed configuration on a catheter and expanded in the desired position by balloon inflation or by utilization of a self-expanding frame or stent. A challenge in catheter-implanted prosthetic valves is control of perivalvular leakage around the valve, which can occur for a period of time following initial implantation. An additional challenge includes the process of crimping such a prosthetic valve to a profile suitable for percutaneous delivery to a subject, as well as for storage and/or delivery to a health care provider.

SUMMARY

Embodiments of a radially collapsible and expandable prosthetic valve are disclosed herein that include an improved outer skirt for controlling perivalvular leakage, as well as methods of crimping, and apparatuses including, such prosthetic valves. In several embodiments, the disclosed prosthetic valves are configured as replacement heart valves for implantation into a subject.

In several embodiments, a radially compressible and expandable prosthetic heart valve is provided comprising an annular frame having an inflow end portion and an outflow end portion, a leaflet structure positioned within the frame, and an annular outer skirt positioned around an outer surface of the frame. The outer skirt comprises an inflow edge radially secured to the frame at a first location, an outflow edge radially secured to the frame at a second location, and an intermediate portion between the inflow edge and the outflow edge. The intermediate portion of the outer skirt comprises slack that buckles or billows radially outward from the inflow and outflow edges of the outer skirt when the prosthetic valve is in the expanded configuration. When the prosthetic valve is collapsed to the collapsed configuration, the axial distance between the inflow edge of the outer skirt and the outflow edge of the outer skirt increases, reducing the slack in the intermediate portion of the outer skirt. The outer skirt can comprise one of (a) a fabric that is stiffer in the axial direction of the valve compared to a circumferential direction to enhance the radial outward buckling of the slack, and/or (b) a self-expandable fabric comprising fibers made of shape memory material having a shape memory set to enhance the radially outward buckling of the slack of the outer skirt.

In embodiments wherein the outer skirt comprises the fabric that is stiffer in the axial direction of the valve compared to a circumferential direction, the outer skirt can comprise a weave of a first set of fibers parallel with the axial direction of the prosthetic valve and a second set of fibers perpendicular to the axial direction of the prosthetic valve. In some embodiments, the fibers in the first set of fibers are stiffer than the fibers in the second set of fibers. The first set of fibers can comprise a set of monofilament fibers. The second set of fibers can comprise a set of microfilament fibers, a set of multifilament fibers, or a set of a microfilament fibers and multifilament fibers. In further embodiments, the second set of fibers comprises fibers that do not comprise residual strain after the prosthetic valve is expanded to the expanded configuration from the collapsed configuration.

In embodiments wherein the outer skirt comprises the self-expandable fabric comprising fibers made of shape memory material, the self-expandable fabric can comprise a weave of warp fibers and weft fibers, wherein one or more of the weft fibers comprise the fibers made of shape memory material. The weave of warp and weft fibers can comprise a combination of multiple weave patters. For example, the weave of warp and weft fibers can comprise a combination of a plain weave pattern comprising warp fibers and weft fibers made of non-shape memory material, and a satin weave pattern comprising warp fibers made of non-shape memory material and weft fibers made of the shape memory material. In some embodiments, the shape memory material can be a nickel titanium alloy, for example, the fibers made of the shape memory material can be nickel titanium wires comprising a diameter of from 0.5 to 15 Mils.

An exemplary embodiment of an assembly for implanting a prosthetic heart valve in a patient's body comprises a delivery apparatus comprising an elongated shaft and a radially expandable prosthetic heart valve mounted on the shaft in a radially collapsed configuration for delivery into the body.

In some embodiments, a method of crimping a prosthetic valve comprises partially inserting the prosthetic valve in the expanded configuration into the crimping jaws of a crimping device, wherein a portion of the prosthetic valve comprising an outer skirt extends outside of the crimper jaws. The prosthetic valve is then crimped to a first partially collapsed configuration, after which the prosthetic valve is fully inserted into the jaws of the crimping device. The prosthetic valve is then crimped to a second partially collapsed configuration, and optionally crimped to a fully collapsed configuration, before removal from the crimping device.

The foregoing and other features and advantages of this disclosure will become more apparent from the following detailed description of several embodiments which proceeds with reference to the accompanying figures.

BRIEF DESCRIPTION OF THE DRAWINGS

FIGS. 4-10 show an exemplary frame of the prosthetic heart valve of FIG. 1.

FIGS. 11-15B show another exemplary frame for use in a prosthetic heart valve.

FIGS. 16A and 16B show an exemplary inner skirt of the prosthetic heart valve of FIG. 1.

FIG. 17 shows another embodiment of a prosthetic heart valve with a deformed frame.

FIG. 18 shows the prosthetic heart valve of FIG. 1 in a collapsed configuration and mounted on an exemplary balloon catheter.

FIGS. 21-28 show the assembly of an exemplary leaflet structure.

FIGS. 29-35 show the assembly of commissure portions of the leaflet structure with window frame portions of the frame.

DETAILED DESCRIPTION

Figure 1:
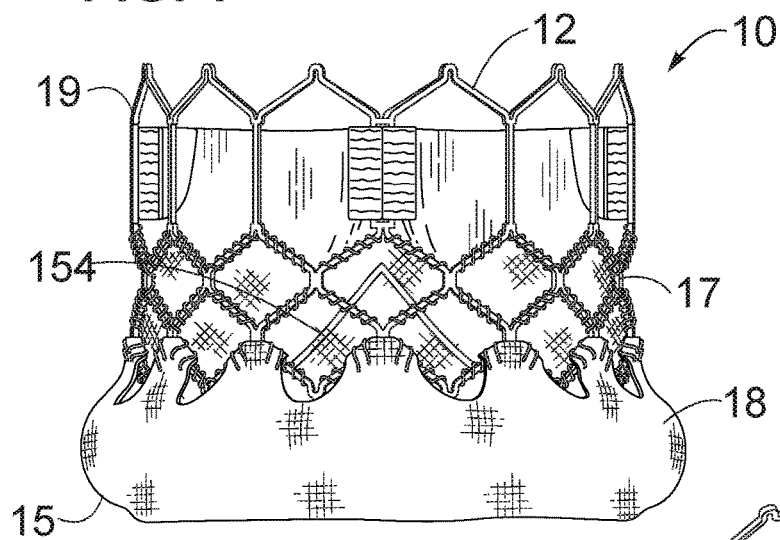
FIGS. 1-3 show an exemplary embodiment of a prosthetic heart valve.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods, systems, and apparatus can be used in conjunction with other systems, methods, and apparatus.

As used herein, the terms "a", "an", and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A", "B", "C", "A and B", "A and C", "B and C", or "A, B, and C".

As used herein, the term "coupled" generally means physically coupled or linked and does not exclude the presence of intermediate elements between the coupled items absent specific contrary language.

Figure 2:
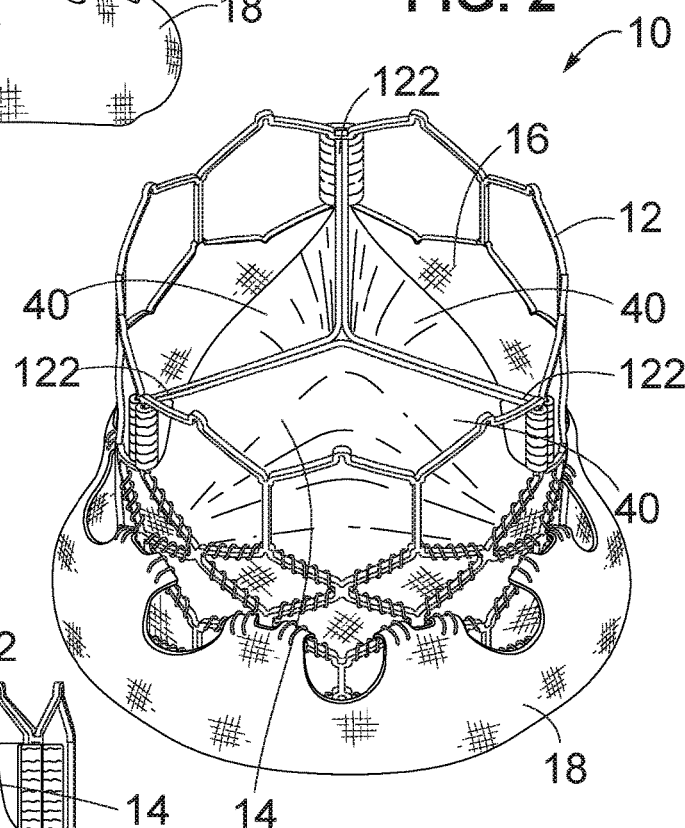
Figure 3:
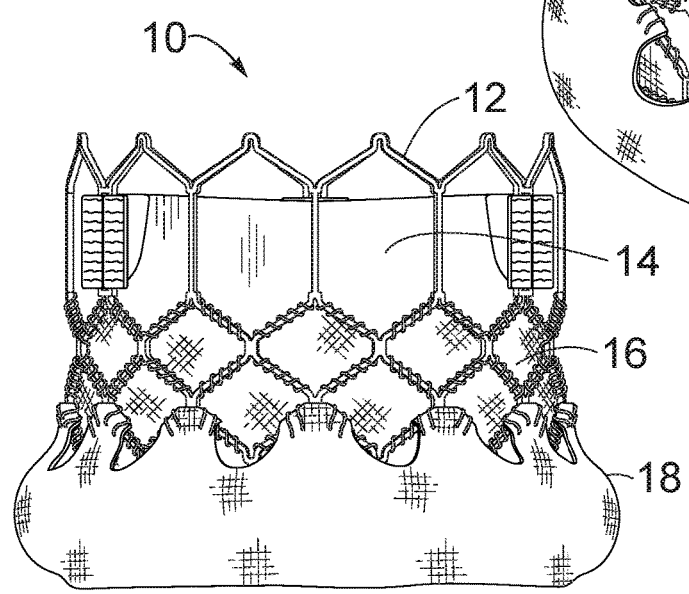
Figure 9:
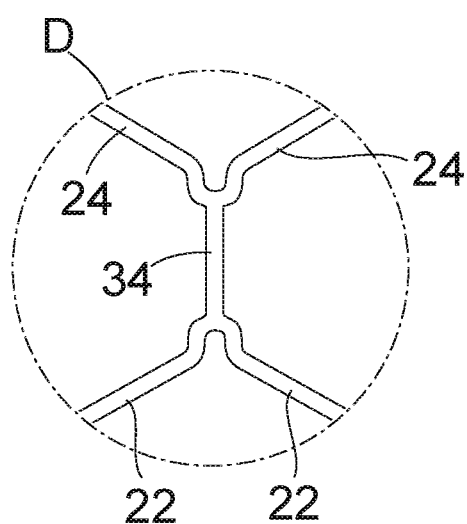
Figure 10:
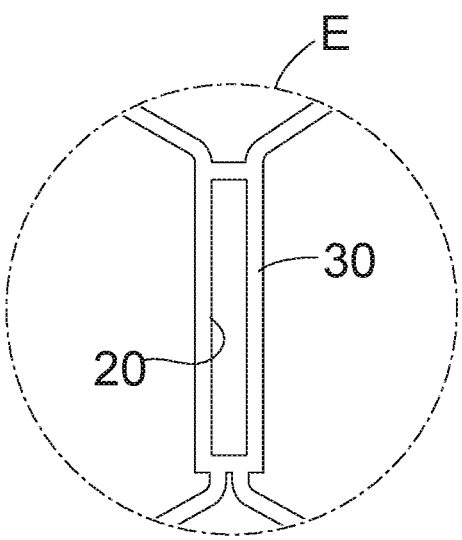

FIGS. 1-3 show various views of a prosthetic heart valve 10, according to one embodiment. The illustrated prosthetic valve is adapted to be implanted in the native aortic annulus, although in other embodiments it can be adapted to be implanted in the other native annuluses of the heart (e.g., the pulmonary, mitral, and tricuspid valves). The prosthetic valve can also be adapted to be implanted in other tubular organs or passageways in the body. The prosthetic valve 10 can have four main components: a stent, or frame, 12, a valvular structure 14, an inner skirt 16, and a perivalvular sealing means, and can have an inflow end portion 15, an intermediate portion 17, and an outflow end portion 19. In the illustrated embodiment, the perivalvular sealing means comprises an outer skirt 18.

The valvular structure 14 can comprise three leaflets 40, collectively forming a leaflet structure, which can be arranged to collapse in a tricuspid arrangement, as best shown in FIG. 2. The lower edge of leaflet structure 14 desirably has an undulating, curved scalloped shape (suture line 154 shown in FIG. 1 tracks the scalloped shape of the leaflet structure). By forming the leaflets with this scalloped geometry, stresses on the leaflets are reduced, which in turn improves durability of the prosthetic valve. Moreover, by virtue of the scalloped shape, folds and ripples at the belly of each leaflet (the central region of each leaflet), which can cause early calcification in those areas, can be eliminated or at least minimized. The scalloped geometry also reduces the amount of tissue material used to form leaflet structure, thereby allowing a smaller, more even crimped profile at the inflow end of the prosthetic valve. The leaflets 40 can be formed of pericardial tissue (e.g., bovine pericardial tissue), biocompatible synthetic materials, or various other suitable natural or synthetic materials as known in the art and described in U.S. Pat. No. 6,730,118, which is incorporated by reference herein.

The bare frame 12 is shown in FIG. 4. The frame 12 can be formed with a plurality of circumferentially spaced slots, or commissure windows, 20 (three in the illustrated embodiment) that are adapted to mount the commissures of the valvular structure 14 to the frame, as described in greater detail below. The frame 12 can be made of any of various suitable plastically-expandable materials (e.g., stainless steel, etc.) or self-expanding materials (e.g., nickel titanium alloy (NiTi), such as nitinol) as known in the art. When constructed of a plastically-expandable material, the frame 12 (and thus the prosthetic valve 10) can be crimped to a radially collapsed configuration on a delivery catheter and then expanded inside a patient by an inflatable balloon or equivalent expansion mechanism. When constructed of a self-expandable material, the frame 12 (and thus the prosthetic valve 10) can be crimped to a radially collapsed configuration and restrained in the collapsed configuration by insertion into a sheath or equivalent mechanism of a delivery catheter. Once inside the body, the prosthetic valve can be advanced from the delivery sheath, which allows the prosthetic valve to expand to its functional size.

Suitable plastically-expandable materials that can be used to form the frame 12 include, without limitation, stainless steel, a biocompatible, high-strength alloys (e.g., a cobalt-chromium or a nickel-cobalt-chromium alloys), polymers, or combinations thereof. In particular embodiments, frame 12 is made of a nickel-cobalt-chromium-molybdenum alloy, such as MP35N® alloy (SPS Technologies, Jenkintown, Pa.), which is equivalent to UNS R30035 alloy (covered by ASTM F562-02). MP35N® alloy/UNS R30035 alloy comprises 35% nickel, 35% cobalt, 20% chromium, and 10% molybdenum, by weight. It has been found that the use of MP35N® alloy to form frame 12 provides superior structural results over stainless steel. In particular, when MP35N® alloy is used as the frame material, less material is needed to achieve the same or better performance in radial and crush force resistance, fatigue resistances, and corrosion resistance. Moreover, since less material is required, the crimped profile of the frame can be reduced, thereby providing a lower profile prosthetic valve assembly for percutaneous delivery to the treatment location in the body.

Referring to FIGS. 4 and 5, the frame 12 in the illustrated embodiment comprises a first, lower row I of angled struts 22 arranged end-to-end and extending circumferentially at the inflow end of the frame; a second row II of circumferentially extending, angled struts 24; a third row III of circumferentially extending, angled struts 26; a fourth row IV of circumferentially extending, angled struts 28; and a fifth row V of circumferentially extending, angled struts 32 at the outflow end of the frame. A plurality of substantially straight axially extending struts 34 can be used to interconnect the struts 22 of the first row I with the struts 24 of the second row II. The fifth row V of angled struts 32 are connected to the fourth row IV of angled struts 28 by a plurality of axially extending window frame portions 30 (which define the commissure windows 20) and a plurality of axially extending struts 31. Each axial strut 31 and each frame portion 30 extends from a location defined by the convergence of the lower ends of two angled struts 32 to another location defined by the convergence of the upper ends of two angled struts 28. FIGS. 6, 7, 8, 9, and 10 are enlarged views of the portions of the frame 12 identified by letters A, B, C, D, and E, respectively, in FIG. 4.

Each commissure window frame portion 30 mounts a respective commissure of the leaflet structure 14. As can be seen each frame portion 30 is secured at its upper and lower ends to the adjacent rows of struts to provide a robust configuration that enhances fatigue resistance under cyclic loading of the prosthetic valve compared to known, cantilevered struts for supporting the commissures of the leaflet structure. This configuration enables a reduction in the frame wall thickness to achieve a smaller crimped diameter of the prosthetic valve. In particular embodiments, the thickness T of the frame 12 (FIG. 4) measured between the inner diameter and outer diameter is about 0.48 mm or less.

The struts and frame portions of the frame collectively define a plurality of open cells of the frame. At the inflow end of the frame 12, struts 22, struts 24, and struts 34 define a lower row of cells defining openings 36. The second, third, and fourth rows of struts 24, 26, and 28 define two intermediate rows of cells defining openings 38. The fourth and fifth rows of struts 28 and 32, along with frame portions 30 and struts 31, define an upper row of cells defining openings 40. The openings 40 are relatively large and are sized to allow portions of the leaflet structure 14 to protrude, or bulge, into and/or through the openings 40 when the frame 12 is crimped in order to minimize the crimping profile.

Figure 45:
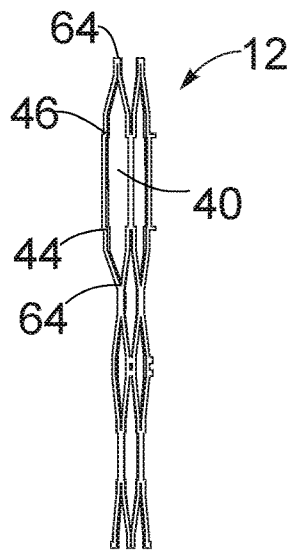
FIG. 45 shows a portion of the frame of FIG. 4 in a radially collapsed configuration.

As best shown in FIG. 7, the lower end of the strut 31 is connected to two struts 28 at a node or junction 44, and the upper end of the strut 31 is connected to two struts 32 at a node or junction 46. The strut 31 can have a thickness S1 that is less than the thicknesses S2 of the junctions 44, 46. FIG. 45 shows a portion of the frame 12 in a collapsed configuration. The junctions 44, 46, along with junctions 64, prevent full closure of openings 40. FIG. 18 shows the prosthetic valve 10 crimped on a balloon catheter. As can be seen, the geometry of the struts 31, and junctions 44, 46, and 64 assists in creating enough space in openings 40 in the collapsed configuration to allow portions of the prosthetic leaflets to protrude or bulge outwardly through openings. This allows the prosthetic valve to be crimped to a relatively smaller diameter than if all of the leaflet material were constrained within the crimped frame.

The frame 12 is configured to reduce, to prevent, or to minimize possible over-expansion of the prosthetic valve at a predetermined balloon pressure, especially at the outflow end portion 19 of the frame, which supports the leaflet structure 14. In one aspect, the frame is configured to have relatively larger angles 42a, 42b, 42c, 42d, 42e between struts, as shown in FIG. 5. The larger the angle, the greater the force required to open (expand) the frame. This phenomenon is schematically illustrated in FIGS. 15A and 15B. FIG. 15A shows a strut 32 when the frame 12 is in its collapsed configuration (e.g., mounted on a balloon). The vertical distance $d_1$ between the ends of the struts is greatest when the frame is compressed, providing a relatively large moment between forces $F_1$ and $F_2$ acting on the ends of the strut in opposite directions upon application of an opening force from inflation of the balloon (or from expansion of another expansion device). When the frame expands radially, the vertical distance between the ends of the strut decreases to a distance $d_2$, as depicted in FIG. 15B. As the vertical distance decreases, so does the moment between forces $F_1$ and $F_2$. Hence, it can be seen that a relatively greater expansion force is required as the vertical distance and the moment between the ends of the strut decreases. Moreover, strain hardening (stiffening) at the ends of the strut increases as the frame expands, which increases the expansion force required to induce further plastic deformation at the ends of the strut. As such, the angles between the struts of the frame can be selected to limit radial expansion of the frame at a given opening pressure (e.g., inflation pressure of the balloon). In particular embodiments, these angles are at least 110 degrees or greater when the frame is expanded to its functional size, and even more particularly these angles are up to about 120 degrees when the frame is expanded to its functional size.

Figure 47:
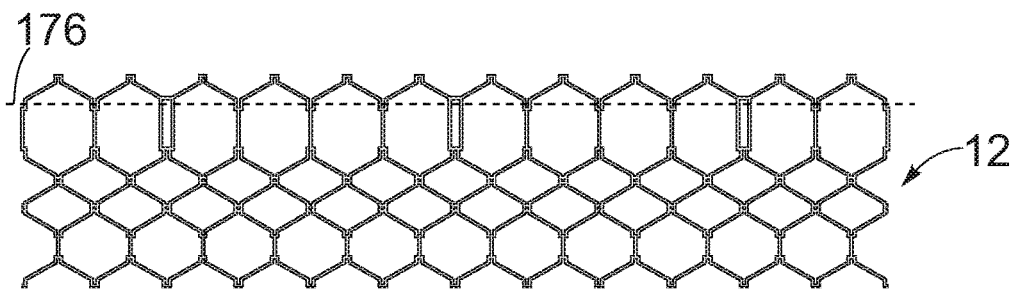
FIG. 47 shows the frame of FIG. 4 in an unrolled, flat configuration.

In addition, the inflow and outflow ends of a frame generally tend to over-expand more so than the middle portion of the frame due to the "dog boning" effect of the balloon used to expand the prosthetic valve. To protect against over-expansion of the leaflet structure 14, the leaflet structure desirably is secured to the frame 12 below the upper row of struts 32, as best shown in FIG. 1. FIG. 47 shows a flattened view of the frame 12 similar to FIG. 5, but showing a dashed line 176 superimposed over the frame to indicate the approximate position of the upper edges of the leaflets 40 in some embodiments. Thus, in the event that the outflow end of the frame is over-expanded, the leaflet structure is positioned at a level below where over-expansion is likely to occur, thereby protecting the leaflet structure from over-expansion.

Figure 48:
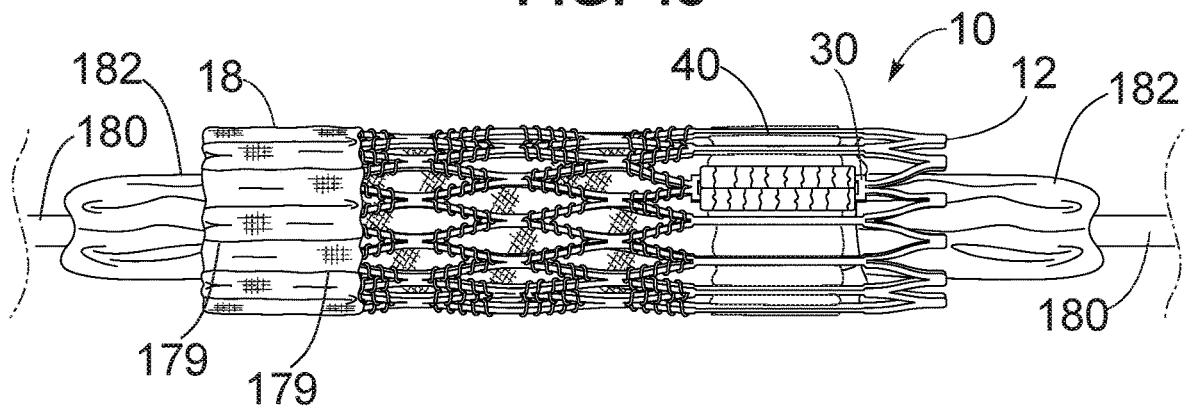
FIG. 48 shows the prosthetic heart valve of FIG. 1 in a collapsed configuration and mounted on an exemplary balloon catheter.

In a known prosthetic valve construction, portions of the leaflets can protrude longitudinally beyond the outflow end of the frame when the prosthetic valve is crimped if the leaflets are mounted too close to the distal end of the frame. If the delivery catheter on which the crimped prosthetic valve is mounted includes a pushing mechanism or stop member that pushes against or abuts the outflow end of the prosthetic valve (for example, to maintain the position of the crimped prosthetic valve on the delivery catheter), the pushing member or stop member can damage the portions of the exposed leaflets that extend beyond the outflow end of the frame. Another benefit of mounting the leaflets at a location spaced away from the outflow end of the frame is that when the prosthetic valve is crimped on a delivery catheter, as shown in FIG. 48, the outflow end of the frame 12 rather than the leaflets 40 is the proximal-most component of the prosthetic valve 10. As such, if the delivery catheter includes a pushing mechanism or stop member that pushes against or abuts the outflow end of the prosthetic valve, the pushing mechanism or stop member contacts the outflow end of the frame, and not leaflets 40, so as to avoid damage to the leaflets.

Figure 46:
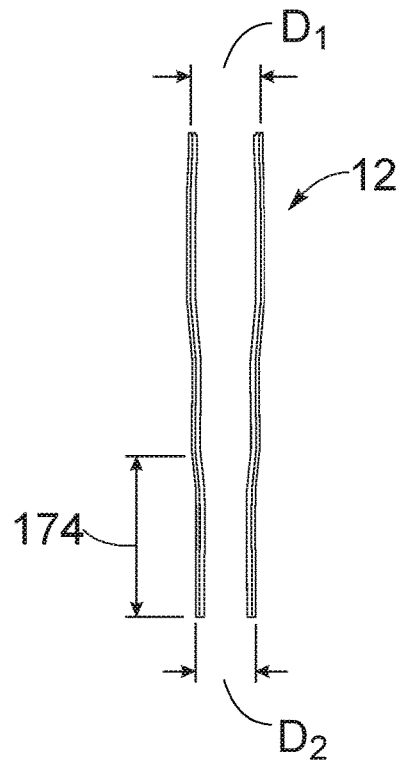
FIG. 46 shows a cross-sectional profile of the frame of FIG. 4, showings a general tapering from the outflow end to the inflow end.

Also, as can be seen in FIG. 5, the openings 36 of the lowermost row of openings in the frame are relatively larger than the openings 38 of the two intermediate rows of openings. As shown in FIG. 46, this allows the frame, when crimped, to assume an overall tapered shape that tapers from a maximum diameter $D_1$ at the outflow end of the prosthetic valve to a minimum diameter $D_2$ at the inflow end of the prosthetic valve. When crimped, the frame 12 has a reduced diameter region extending along a portion of the frame adjacent the inflow end of the frame, indicated by reference number 174, that generally corresponds to the region of the frame covered by the outer skirt 18. In some embodiments, the diameter of region 174 is reduced compared to the diameter of the upper portion of the frame (which is not covered by the outer skirt) such that the outer skirt 18 does not increase the overall crimp profile of the prosthetic valve. When the prosthetic valve is deployed, the frame can expand to the generally cylindrical shape shown in FIG. 4. In one example, the frame of a 26-mm prosthetic valve, when crimped, had a diameter $D_1$ of 14 French at the outflow end of the prosthetic valve and a diameter $D_2$ of 12 French at the inflow end 174 of the prosthetic valve.

Figure 11:
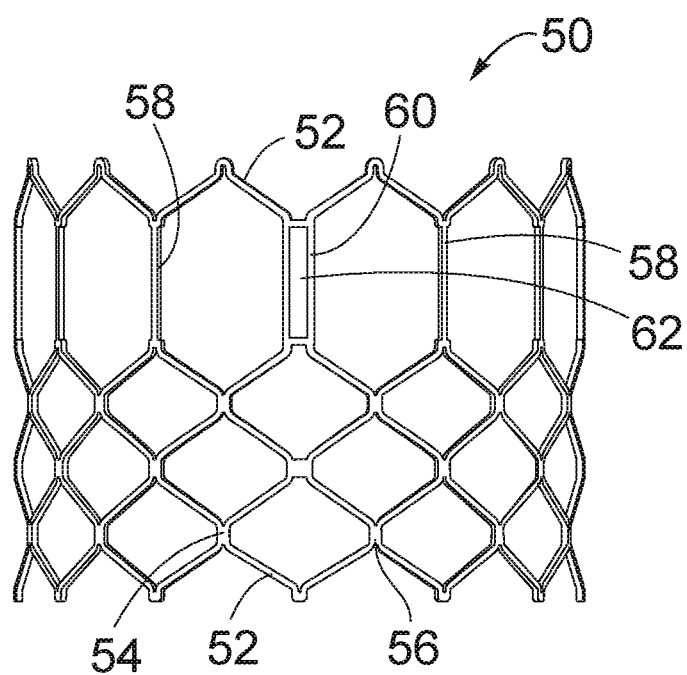

FIGS. 11 and 12 show an alternative frame 50 that can be incorporated in the prosthetic valve 10. The frame 50 comprises multiple rows of circumferentially extending, angled struts 52 that are connected to each other at nodes, or connecting portions, 54 and 56. The uppermost row of struts 52 are connected to an adjacent row of struts by a plurality of axially extending struts 58 and commissure window frame portions 60. Each commissure frame portion 60 defines a slot, or commissure window, 62 for mounting a respective commissure of the valvular structure, as described in greater detail below. In particular embodiments, the thickness T of the frame 50 is about 0.45 mm or less. Of course, the thickness T of the frame is selected to provide sufficient strength to the frame. As such, those skilled in the art will understand that the thickness T differs for different sub-components and/or assemblies of the frame in some embodiments. FIGS. 13 and 14 are enlarged views of the portions of the frame 50 identified by letters A and B, respectively, in FIG. 12.

The main functions of the inner skirt 16 are to assist in securing the valvular structure 14 to the frame 12 and to assist in forming a good seal between the prosthetic valve and the native annulus by blocking the flow of blood through the open cells of the frame 12 below the lower edge of the leaflets. The inner skirt 16 desirably comprises a tough, tear resistant material such as polyethylene terephthalate (PET), although various other synthetic or natural materials can be used. The thickness of the skirt desirably is less than about 0.15 mm (about 6 mil), and desirably less than about 0.1 mm (about 4 mil), and even more desirably about 0.05 mm (about 2 mil). In particular embodiments, the skirt 16 can have a variable thickness, for example, the skirt can be thicker at least one of its edges than at its center. In one implementation, the skirt 16 can comprise a PET skirt having a thickness of about 0.07 mm at its edges and about 0.06 mm at its center. The thinner skirt can provide for better crimping performances while still providing good perivalvular sealing.

Figure 38:
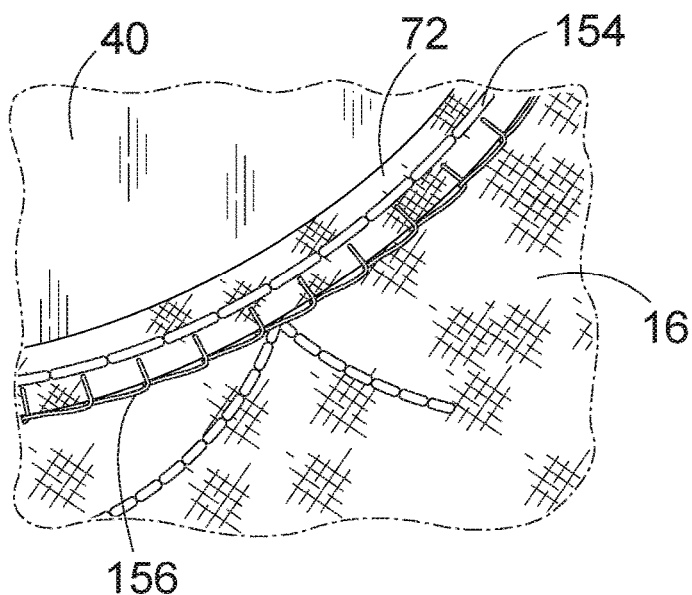
Figure 39:
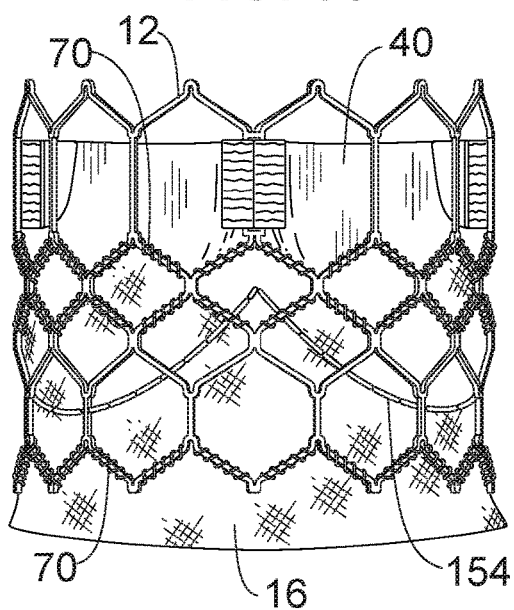

The skirt 16 can be secured to the inside of frame 12 via sutures 70, as shown in FIG. 39. Valvular structure 14 can be attached to the skirt via one or more reinforcing strips 72 (which collectively can form a sleeve), for example thin, PET reinforcing strips, discussed below, which enables a secure suturing and protects the pericardial tissue of the leaflet structure from tears. Valvular structure 14 can be sandwiched between skirt 16 and the thin PET strips 72 as shown in FIG. 38. Sutures 154, which secure the PET strip and the leaflet structure 14 to skirt 16, can be any suitable suture, such as Ethibond Excel® PET suture (Johnson & Johnson, New Brunswick, N.J.). Sutures 154 desirably track the curvature of the bottom edge of leaflet structure 14, as described in more detail below.

Known fabric skirts comprise a weave of warp and weft fibers that extend perpendicularly to each other and with one set of the fibers extending longitudinally between the upper and lower edges of the skirt. When the metal frame to which the fabric skirt is secured is radially compressed, the overall axial length of the frame increases. Unfortunately, a fabric skirt, which inherently has limited elasticity, cannot elongate along with the frame and therefore tends to deform the struts of the frame and to prevent uniform crimping.

Referring to FIG. 16B, in contrast to known fabric skirts, the skirt 16 desirably is woven from a first set of fibers, or yarns or strands, 78 and a second set of fibers, or yarns or strands, 80, both of which are non-perpendicular to the upper edge 82 and the lower edge 84 of the skirt. In particular embodiments, the first set of fibers 78 and the second set of fibers 80 extend at angles of about 45 degrees relative to the upper and lower edges 82, 84. The skirt 16 can be formed by weaving the fibers at 45 degree angles relative to the upper and lower edges of the fabric. Alternatively, the skirt can be diagonally cut (cut on a bias) from a vertically woven fabric (where the fibers extend perpendicularly to the edges of the material) such that the fibers extend at 45 degree angles relative to the cut upper and lower edges of the skirt. As further shown in FIG. 16B, the opposing short edges 86, 88 of the skirt desirably are non-perpendicular to the upper and lower edges 82, 84. For example, the short edges 86, 88 desirably extend at angles of about 45 degrees relative to the upper and lower edges and therefore are aligned with the first set of fibers 78. Therefore the overall general shape of the skirt is that of a rhomboid or parallelogram.

FIG. 17 shows an example of a crimped prosthetic valve where the struts have been deformed in several locations, as indicated by reference number 100, by a skirt having fibers that extend perpendicular to and/or longitudinally between the upper and lower edges of the skirt. Moreover, the fabric tends to bunch or create bulges of excess material in certain locations, which limits the minimum crimping profile and prevents uniform crimping.

Figure 19A:
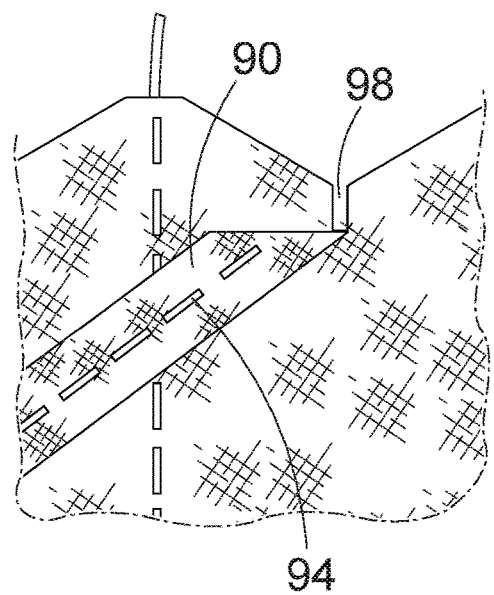
FIGS. 19A, 19B and 20 show the assembly of the inner skirt of FIG. 16A with the frame of FIG. 4.
Figure 19B:
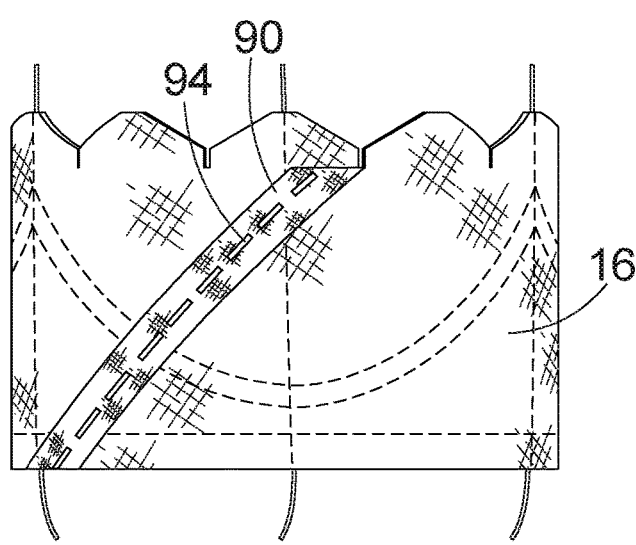
Figure 20:
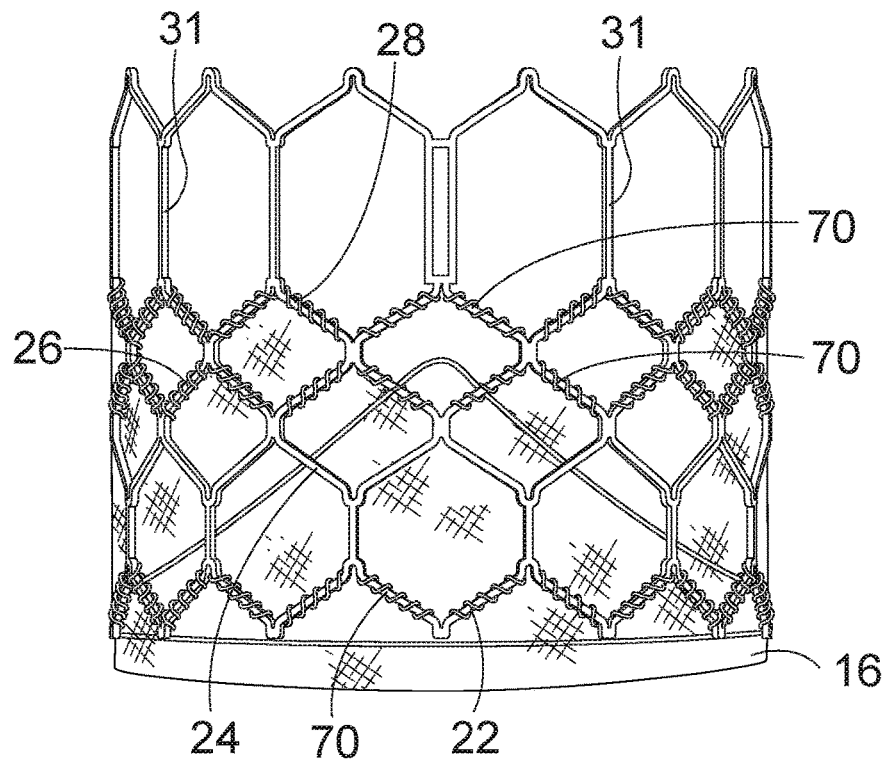

FIGS. 19A and 19B show the skirt 16 after opposing short edge portions 90, 92 have been sewn together to form the annular shape of the skirt. As shown, the edge portion 90 can be placed in an overlapping relationship relative to the opposite edge portion 92, and the two edge portions can be sewn together with a diagonally extending suture line 94 that is parallel to short edges 86, 88. The upper edge portion of the skirt 16 can be formed with a plurality of projections 96 that define an undulating shape that generally follows the shape or contour of the fourth row of struts 28 immediately adjacent the lower ends of axial struts 31. In this manner, as best shown in FIG. 20, the upper edge of skirt 16 can be tightly secured to struts 28 with sutures 70. Skirt 16 can also be formed with slits 98 to facilitate attachment of the skirt to the frame. Slits 98 are dimensioned so as to allow an upper edge portion of skirt to be partially wrapped around struts 28 and to reduce stresses in the skirt during the attachment procedure. For example, in the illustrated embodiment, skirt 16 is placed on the inside of frame 12 and an upper edge portion of the skirt is wrapped around the upper surfaces of struts 28 and secured in place with sutures 70. Wrapping the upper edge portion of the skirt around struts 28 in this manner provides for a stronger and more durable attachment of the skirt to the frame. The skirt 16 can also be secured to the first, second, and third rows of struts 22, 24, and 26, respectively, with sutures 70.

Referring again to FIG. 16B, due to the angled orientation of the fibers relative to the upper and lower edges, the skirt can undergo greater elongation in the axial direction (i.e., in a direction from the upper edge 82 to the lower edge 84).

Thus, when the metal frame 12 is crimped (as shown in FIG. 18), the skirt 16 can elongate in the axial direction along with the frame and therefore provide a more uniform and predictable crimping profile. Each cell of the metal frame in the illustrated embodiment includes at least four angled struts that rotate towards the axial direction on crimping (e.g., the angled struts become more aligned with the length of the frame). The angled struts of each cell function as a mechanism for rotating the fibers of the skirt in the same direction of the struts, allowing the skirt to elongate along the length of the struts. This allows for greater elongation of the skirt and avoids undesirable deformation of the struts when the prosthetic valve is crimped.

In addition, the spacing between the woven fibers or yarns can be increased to facilitate elongation of the skirt in the axial direction. For example, for a PET skirt 16 formed from 20-denier yarn, the yarn density can be about 15% to about 30% lower than in a typical PET skirt. In some examples, the yarn spacing of the skirt 16 can be from about 60 yarns per cm (about 155 yarns per inch) to about 70 yarns per cm (about 180 yarns per inch), such as about 63 yarns per cm (about 160 yarns per inch), whereas in a typical PET skirt the yarn spacing can be from about 85 yarns per cm (about 217 yarns per inch) to about 97 yarns per cm (about 247 yarns per inch). The oblique edges 86, 88 promote a uniform and even distribution of the fabric material along inner circumference of the frame during crimping so as to reduce or minimize bunching of the fabric to facilitate uniform crimping to the smallest possible diameter. Additionally, cutting diagonal sutures in a vertical manner may leave loose fringes along the cut edges. The oblique edges 86, 88 help minimize this from occurring. As noted above, FIG. 17 shows a crimped prosthetic valve with a typical skirt that has fibers that run perpendicularly to the upper and lower edges of the skirt. Comparing FIGS. 17 and 18, it is apparent that the construction of skirt 16 avoids undesirable deformation of the frame struts and provides more uniform crimping of the frame.

In alternative embodiments, the skirt can be formed from woven elastic fibers that can stretch in the axial direction during crimping of the prosthetic valve. The warp and weft fibers can run perpendicularly and parallel to the upper and lower edges of the skirt, or alternatively, they can extend at angles between 0 and 90 degrees relative to the upper and lower edges of the skirt, as described above.

The inner skirt 16 can be sutured to the frame 12 at locations away from the suture line 154 so that the skirt can be more pliable in that area (see FIG. 28, where the suture line follows the marking suture 136, as discussed below). This configuration can avoid stress concentrations at the suture line 154, which attaches the lower edges of the leaflets to the skirt 16.

Figure 21:
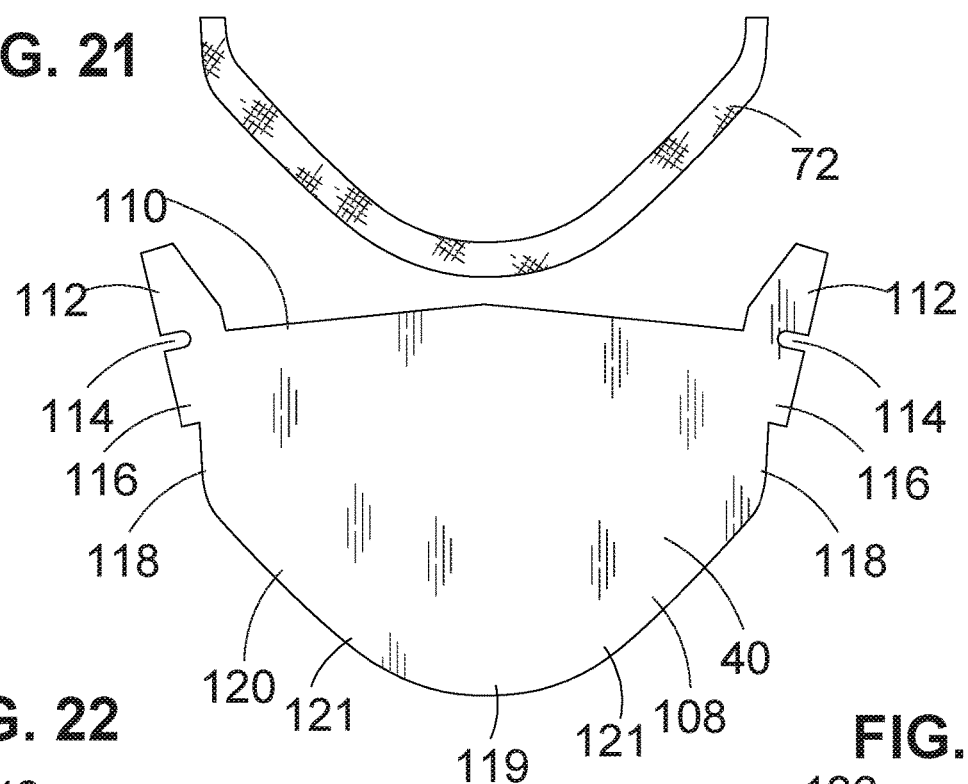
Figure 22:
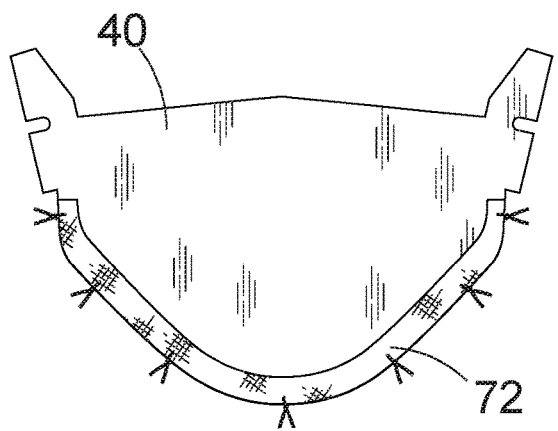

As noted above, the leaflet structure 14 in the illustrated embodiment includes three flexible leaflets 40 (although a greater or a smaller number of leaflets can be used). As best shown in FIG. 21, each leaflet 40 in the illustrated configuration has an upper (outflow) free edge 110 extending between opposing upper tabs 112 on opposite sides of the leaflet. Below each upper tab 112 there is a notch 114 separating the upper tab from a corresponding lower tab 116. The lower (inflow) edge portion 108 of the leaflet extending between respective ends of the lower tabs 116 includes vertical, or axial, edge portions 118 on opposites of the leaflets extending downwardly from corresponding lower tabs 116 and a substantially V-shaped, intermediate edge portion 120 having a smooth, curved apex portion 119 at the lower end of the leaflet and a pair of oblique portions 121 that extend between the axial edge portions and the apex portion. The oblique portions can have a greater radius of curvature than the apex portion. Each leaflet 40 can have a reinforcing strip 72 secured (e.g., sewn) to the inner surface of the lower edge portion 108, as shown in FIG. 22.

Figure 23:
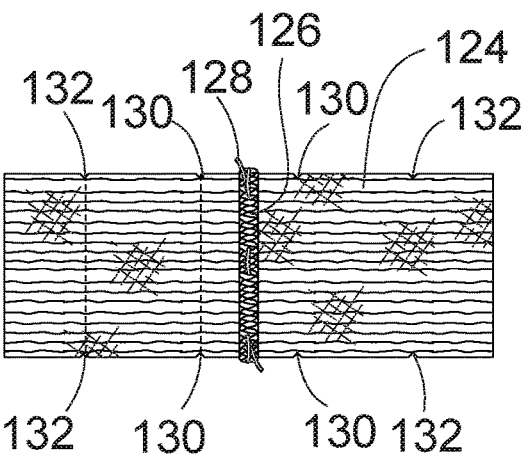

The leaflets 40 can be secured to one another at their adjacent sides to form commissures 122 of the leaflet structure. A plurality of flexible connectors 124 (one of which is shown in FIG. 23) can be used to interconnect pairs of adjacent sides of the leaflets and to mount the leaflets to the commissure window frame portions 30. The flexible connectors 124 can be made from a piece of woven PET fabric, although other synthetic and/or natural materials can be used. Each flexible connector 124 can include a wedge 126 extending from the lower edge to the upper edge at the center of the connector. The wedge 126 can comprise a non-metallic material, such as a rope, a braided yarn, or a monofilament yarn, for example, Ethibond Excel® 2-0 suture material (Johnson & Johnson, New Brunswick, N.J.), secured to the connector with a temporary suture 128. The wedge 126 helps prevent rotational movement of the leaflet tabs once they are secured to the commissure window frame portions 30. The connector 124 can have a series of inner notches 130 and outer notches 132 formed along its upper and lower edges.

Figure 24:
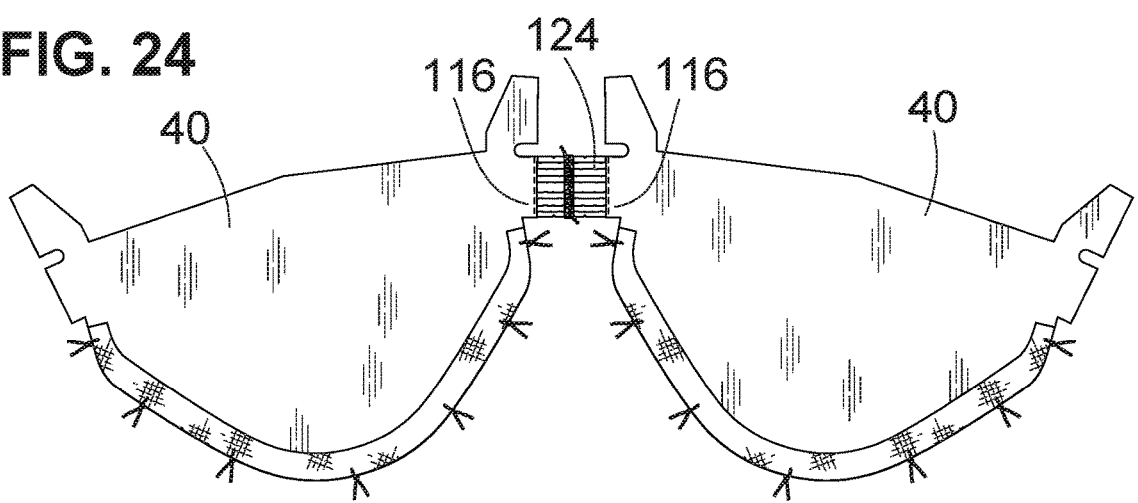
Figure 25:
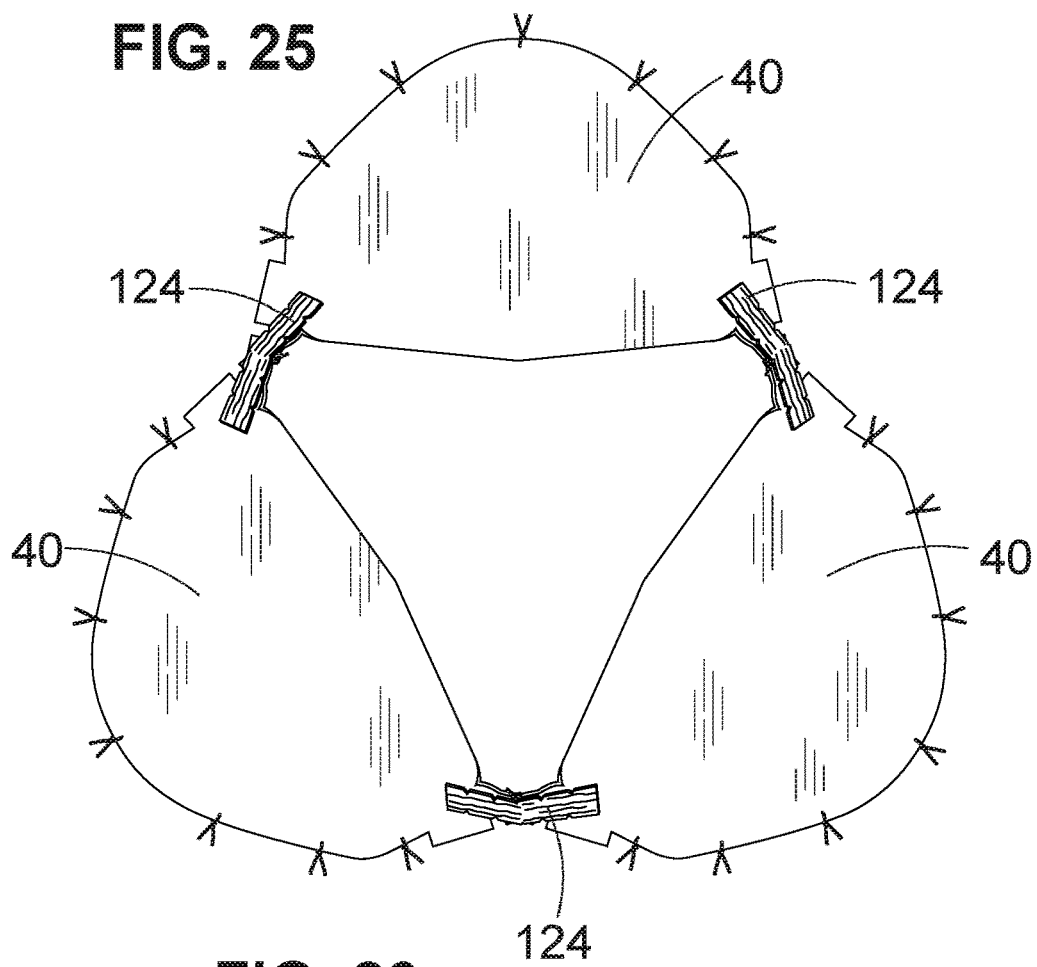

FIG. 24 shows the adjacent sides of two leaflets 40 interconnected by a flexible connector 124. The opposite end portions of the flexible connector 124 can be placed in an overlapping relationship with the lower tabs 116 with the inner notches 130 aligned with the vertical edges of the tabs 116. Each tab 116 can be secured to a corresponding end portion of the flexible connector 124 by suturing along a line extending from an outer notch 132 on the lower edge to an outer notch 132 on the upper edge of the connector. Three leaflets 40 can be secured to each other side-to-side using three flexible connectors 124, as shown in FIG. 25.

Figure 26:
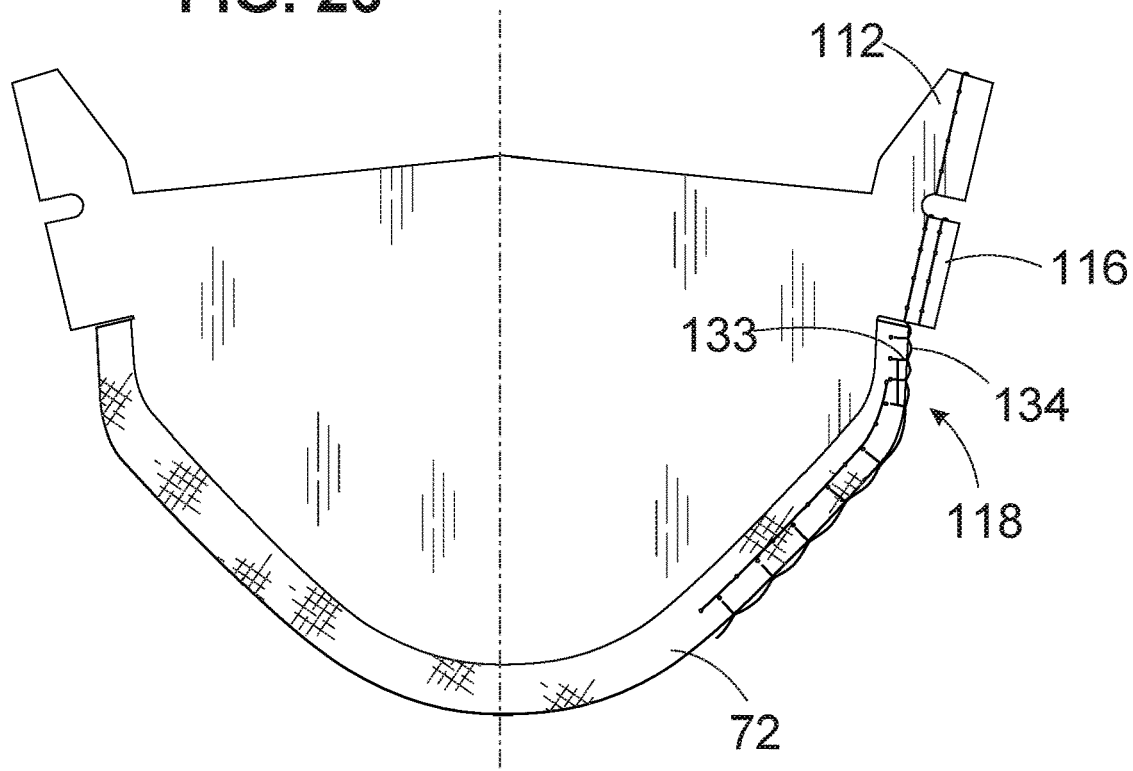

Referring now to FIGS. 26 and 27, the adjacent sub-commissure portions 118 of two leaflets can be sutured directly to each other. In the example shown, PTFE 6-0 suture material is used to form in-and-out stitches and comb stitches 133, 134 that extend through the sub-commissure portions 118 and the reinforcing strips 72 on both leaflets. The two remaining pairs of adjacent sub-commissure portions 118 can be sutured together in the same manner to form the assembled leaflet structure 14, which can then be secured to the frame 12 in the following manner.

As noted above, the inner skirt 16 can be used to assist in suturing the leaflet structure 14 to the frame. As shown in FIG. 28, the skirt 16 can have an undulating temporary marking suture 136 to guide the attachment of the lower edges of each leaflet 40. The skirt 16 itself can be sutured to the struts of the frame 12 using sutures 70, as noted above, before securing the leaflet structure 14 to the skirt 16. The struts that intersect the marking suture 136 desirably are not attached to the skirt 16. This allows the skirt 16 to be more pliable in the areas not secured to the frame and minimizes stress concentrations along the suture line that secures the lower edges of the leaflets to the skirt. The portion of the skirt 16 demarcated by rectangle 140 initially is left unsecured to the frame 12, and is later secured to the frame after the leaflet structure 14 is secured to the skirt, as further described below. As noted above, when the skirt is secured to the frame, the fibers 78, 80 of the skirt (see FIG. 16B) generally align with the angled struts of the frame to promote uniform crimping and expansion of the frame.

Figure 30:
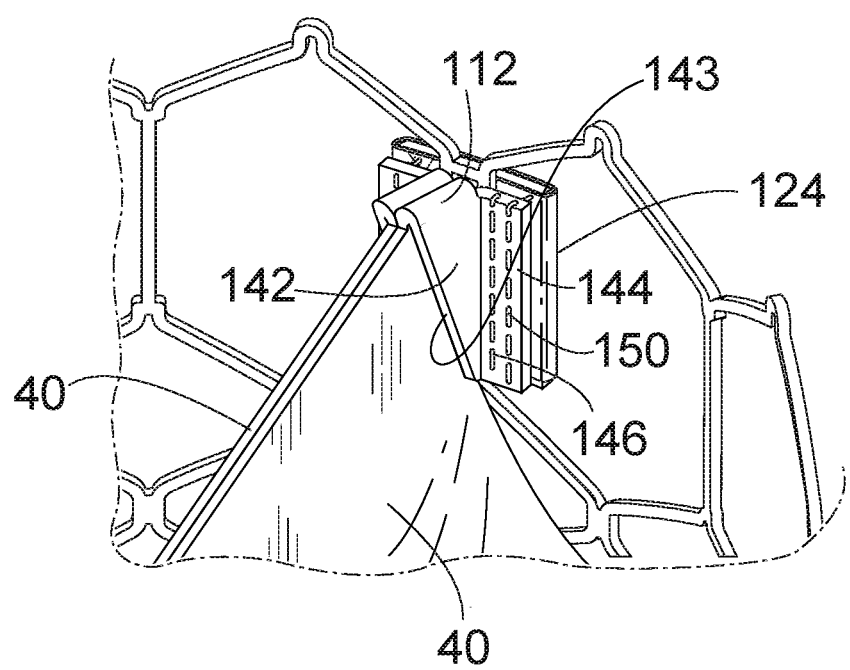
Figure 31:
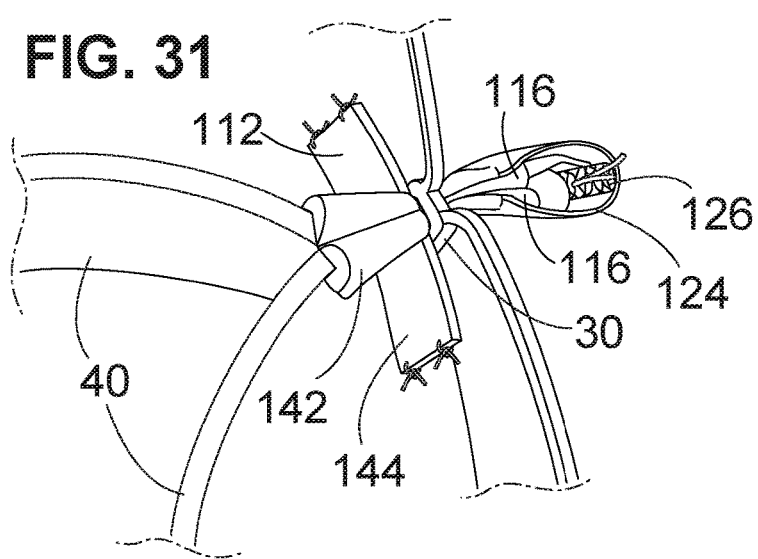
Figure 32:
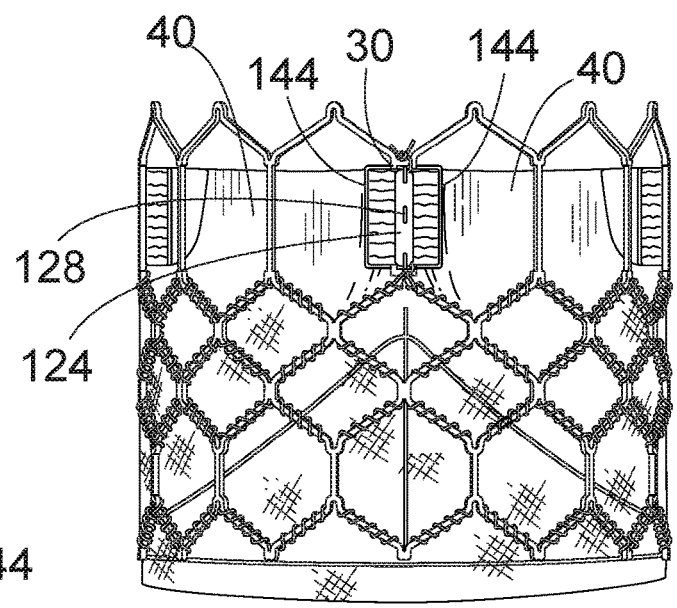

FIG. 29 is a cross-sectional view of a portion of the frame and leaflet structure showing the adjacent tab portions of two leaflets secured to a corresponding window frame portion 30. FIGS. 30-36 show one specific approach for securing the commissure portions 122 of the leaflet structure 14 to the commissure window frame portions 30 of the frame. First, as shown in FIG. 30, the flexible connector 124 securing two adjacent sides of two leaflets is folded widthwise and the upper tab portions 112 are folded downwardly against the flexible connector. As best shown in FIGS. 30 and 31, each upper tab portion 112 is creased lengthwise (vertically) to assume an L-shape having an inner portion 142 folded against the inner surface of the leaflet and an outer portion 144 folded against the connector 124. The outer portion 144 can then be sutured to the connector 124 along a suture line 146. Next, as shown in FIG. 31, the commissure tab assembly (comprised of a pair of lower tab portions 116 connected by connector 124) is inserted through the commissure window 20 of a corresponding window frame portion 30. FIG. 32 is a side view of the frame 12 showing the commissure tab assembly extending outwardly through the window frame portion 30.

Figure 33:
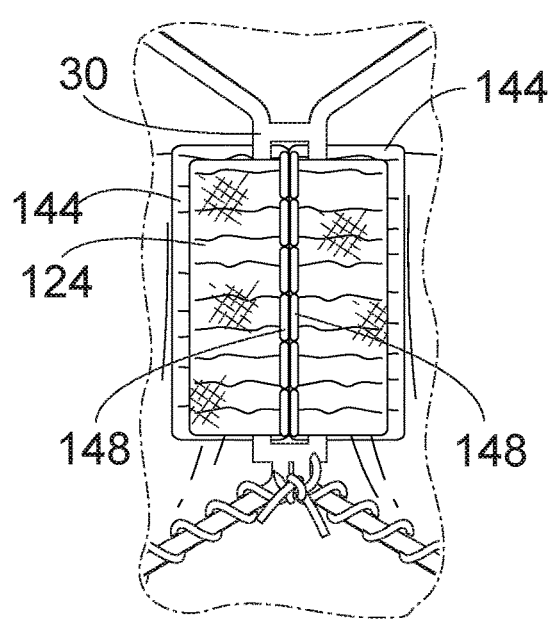
Figure 34:
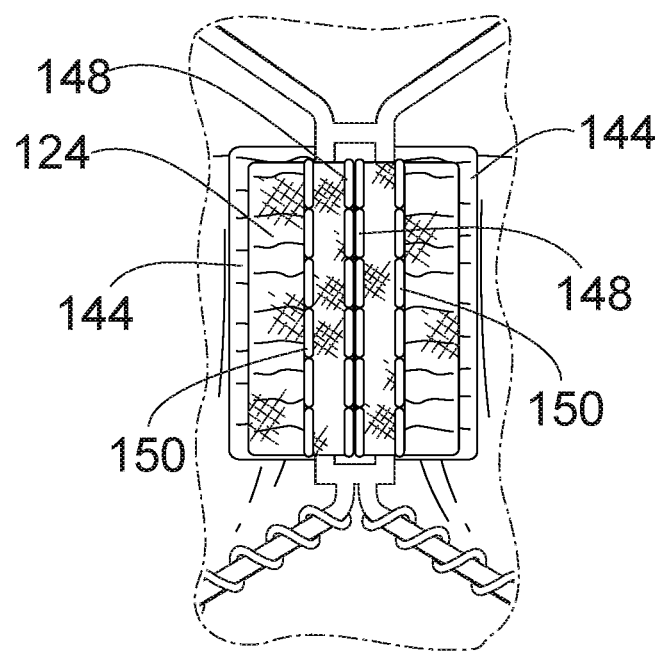
Figure 35:
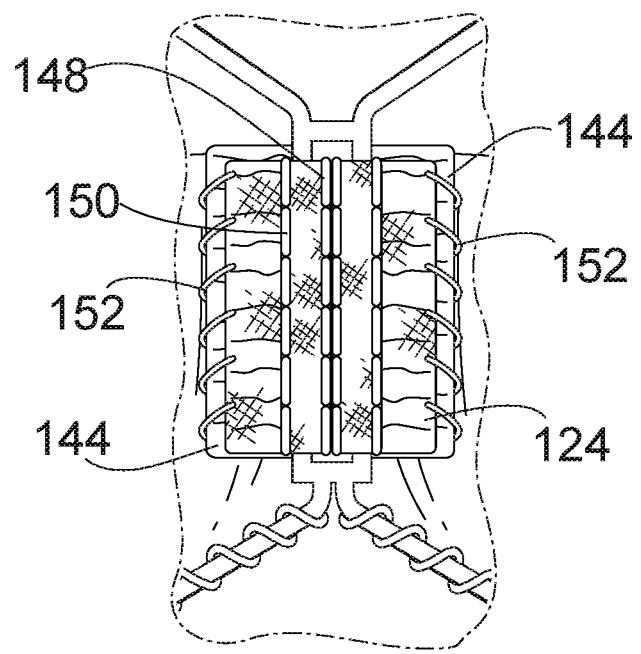

As best shown in FIGS. 29 and 33, the commissure tab assembly is pressed radially inwardly at the wedge 126 such that one of the lower tab portions 116 and a portion of the connector 124 is folded against the frame 12 on one side of the window frame portion 30 and the other lower tab portion 116 and a portion of the connector 124 is folded against the frame 12 on other side of the window frame portion 30. A pair of suture lines 148 is formed to retain the lower tab portions 116 against the frame 12 in the manner shown in FIG. 29. Each suture line 148 extends through connector 124, a lower tab portion 116, the wedge 126, and another portion of connector 124. Then, as shown in FIGS. 29 and 34, each lower tab portion 116 is secured to a corresponding upper tab portion 112 with a primary suture line 150 that extends through one layer of connector 124, the lower tab portion 116, another layer of connector 124, another layer of connector 124, and the upper tab portion 112. Finally, as shown in FIGS. 29 and 35, the suture material used to form the primary suture line 150 can be used to further form whip stitches 152 at the edges of the tab portions 112, 116 that extend through two layers of connector 124 sandwiched between tab portions 112, 116.

As shown in FIGS. 29 and 30, the folded down upper tab portions 112 form a double layer of leaflet material at the commissures. The inner portions 142 of the upper tab portions 112 are positioned flat, abutting layers of the two leaflets 40 forming the commissures, such that each commissure comprises four layers of leaflet material just inside of the window frames 30. This four-layered portion of the commissures can be more resistant to bending, or articulating, than the portion of the leaflets 40 just radially inward from the relatively more-rigid four-layered portion. This causes the leaflets 40 to articulate primarily at inner edges 143 of the folded-down inner portions 142 in response to blood flowing through the prosthetic valve during operation within the body, as opposed to articulating about or proximal to the axial struts of the window frames 30. Because the leaflets articulate at a location spaced radially inwardly from the window frames 30, the leaflets can avoid contact with and damage from the frame. However, under high forces, the four layered portion of the commissures can splay apart about a longitudinal axis 145 (FIG. 29) adjacent to the window frame 30, with each inner portion 142 folding out against the respective outer portion 144. For example, this can occur when the prosthetic valve 10 is compressed and mounted onto a delivery shaft, allowing for a smaller crimped diameter. The four-layered portion of the commissures can also splay apart about axis 145 when the balloon catheter is inflated during expansion of the prosthetic valve, which can relieve some of the pressure on the commissures caused by the balloon, reducing potential damage to the commissures during expansion.

Figure 36:
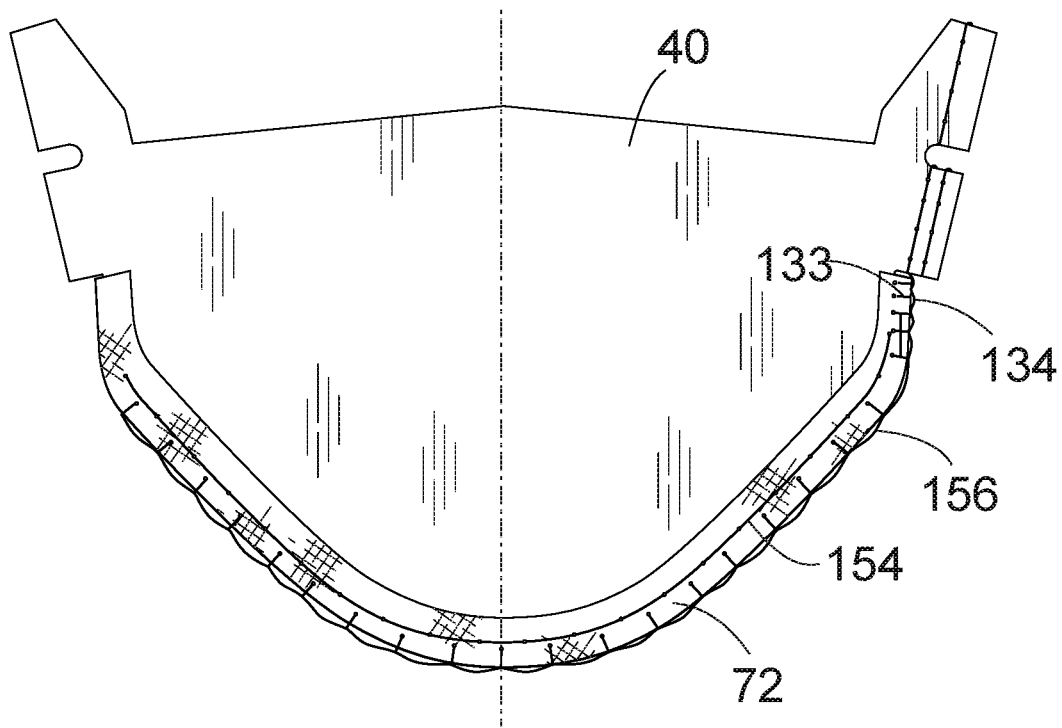
FIGS. 36-40 show the assembly of the leaflet structure with the inner skirt along a lower edge of the leaflets.
Figure 37:
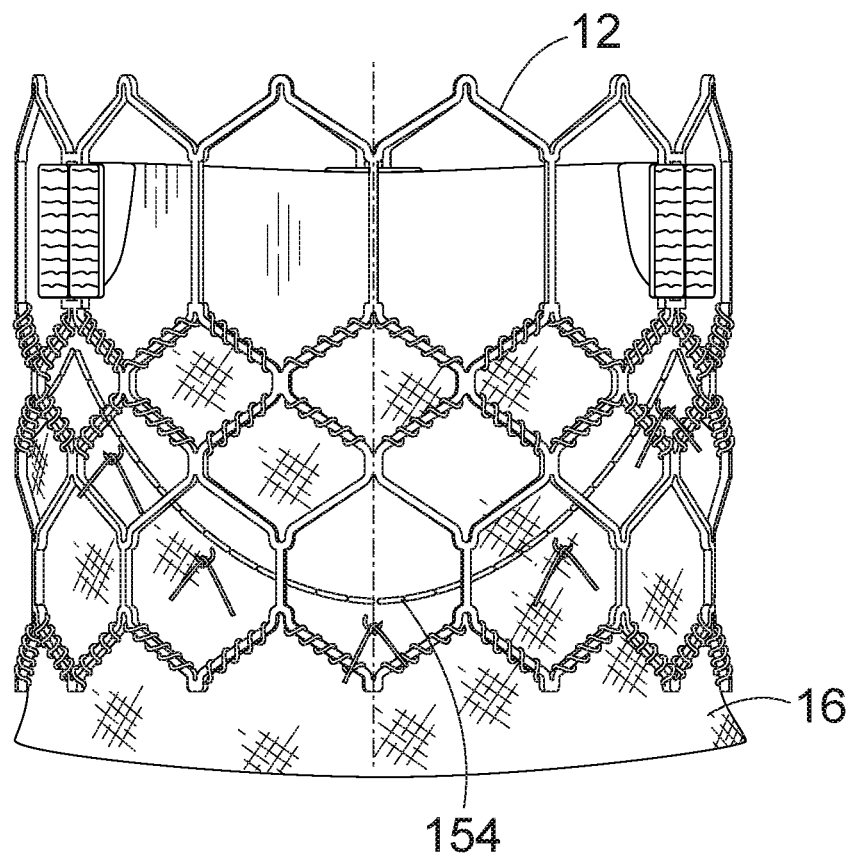
Figure 40:
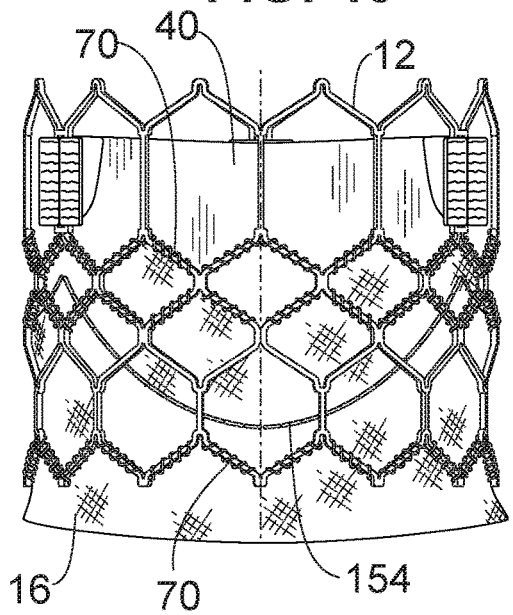

After all three commissure tab assemblies are secured to respective window frame portions 30, the lower edges of the leaflets 40 between the commissure tab assemblies can be sutured to the inner skirt 16. For example, as shown in FIGS. 36-38, each leaflet 40 can be sutured to the skirt 16 along suture line 154 using, for example, Ethibond Excel® PET thread. The sutures can be in-and-out sutures extending through each leaflet 40, the skirt 16, and each reinforcing strip 72. Each leaflet 40 and respective reinforcing strip 72 can be sewn separately to the skirt 16. In this manner, the lower edges of the leaflets are secured to the frame 12 via the skirt 16. As shown in FIG. 38, the leaflets can be further secured to the skirt with blanket sutures 156 that extend through each reinforcing strip 72, leaflet 40 and the skirt 16 while looping around the edges of the reinforcing strips 72 and leaflets 40. The blanket sutures 156 can be formed from PTFE suture material. FIGS. 39 and 40 show two rotated side views of the frame 12, leaflet structure 14 and the skirt 16 after securing the leaflet structure and the skirt to the frame and the leaflet structure to the skirt.

Figure 41:
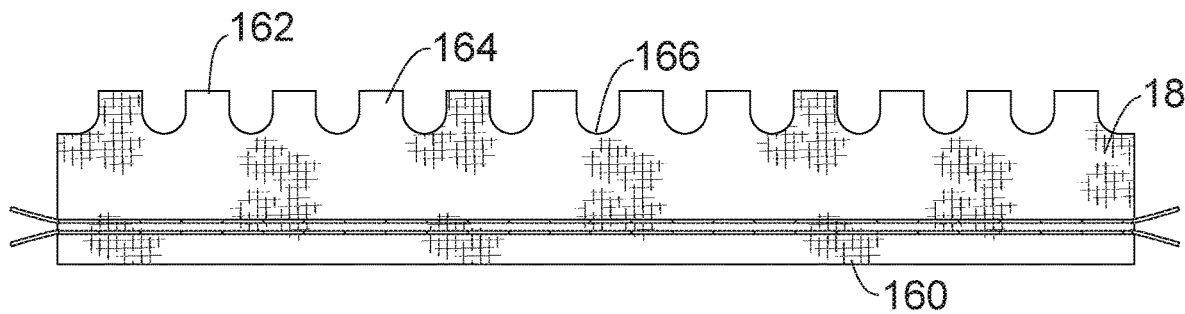
FIG. 41 shows a flattened view of an exemplary outer skirt.
Figure 42:
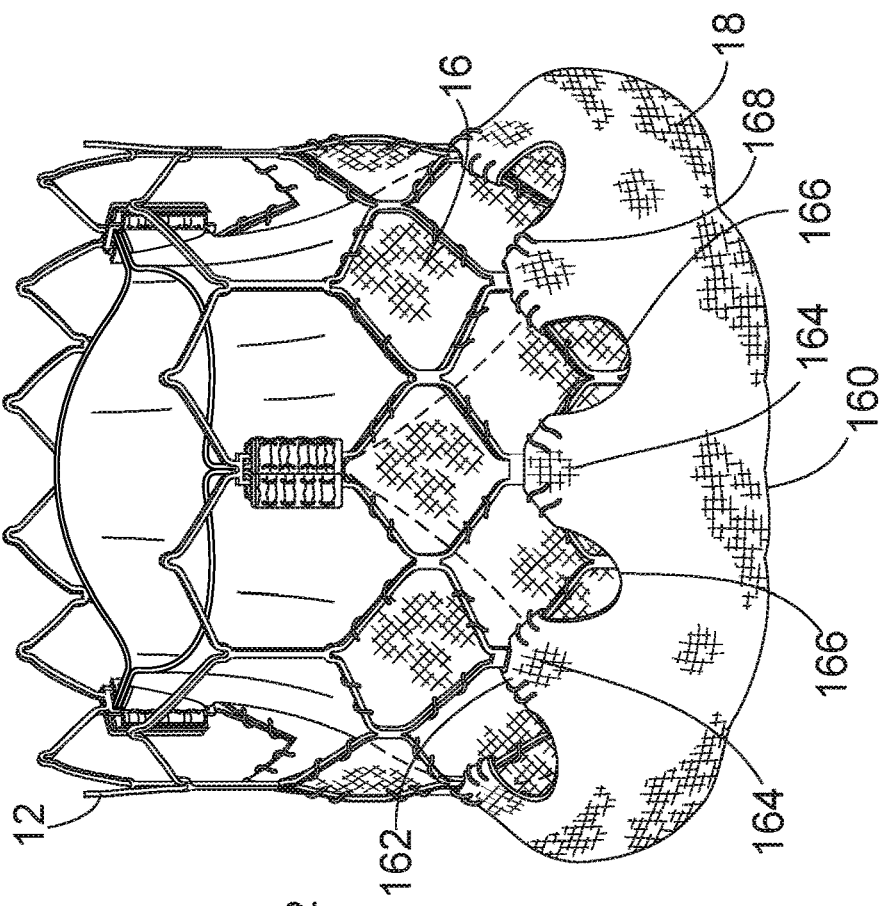
FIGS. 42 and 43 show the exemplary prosthetic heart valve of FIG. 1.
Figure 43:
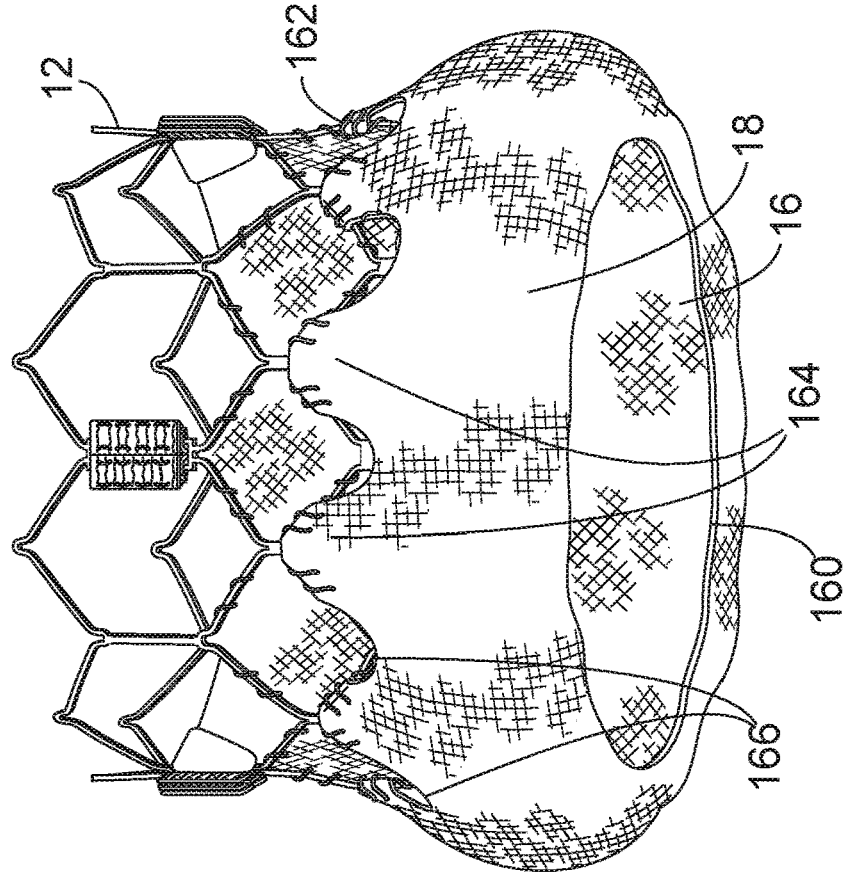

FIG. 41 shows a flattened view of the outer skirt 18 prior to its attachment to the frame 12. The outer skirt 18 can be laser cut or otherwise formed from a strong, durable piece of material. The outer skirt 18 can have a substantially straight lower edge 160 and an upper edge 162 defining a plurality of alternating projections 164 and notches 166, or castellations. As best shown in FIG. 42, the lower edge 160 of the skirt 18 can be sutured to the lower edge of the inner skirt 16 at the inflow end of the prosthetic valve. As shown in FIG. 43, each projection 164 can be sutured to the second rung II of struts 24 of the frame 12. The upper edges 162 of the projections 164 can be folded over respective struts of rung II and secured with sutures 168.

As can be seen in FIGS. 1-3 and 42-43, the outer skirt 18 is secured to the frame 12 such that when the frame is in its expanded configuration (e.g., when deployed in a subject), there is excess material between the lower edge 160 and the upper edge 162 that does not lie flat against the outer surface of the frame 12. The outer skirt 18 can be secured directly to frame 12 and/or indirectly to frame 12, for example, by securing the outer skirt to the inner skirt, which is directly secured to the frame 12. In the expanded configuration of the prosthetic valve, the distance between the upper and lower attachment points of the outer skirt 18 decreases (foreshortens), resulting in outward radial buckling of the outer skirt 18. Additionally, the excess material between the lower and upper edges of the outer skirt 18 allows the frame 12 to elongate axially when crimped without any resistance from the outer skirt. In some embodiments, the skirt 18 includes an axial length or height that can be substantially the same as the axial length between the upper and lower attachment points of the skirt 18 to the frame 12 when the frame is fully crimped. In such embodiments, when the frame 12 is fully crimped, the outer skirt can lie flat against the outer surface of the frame 12.

Figure 44:
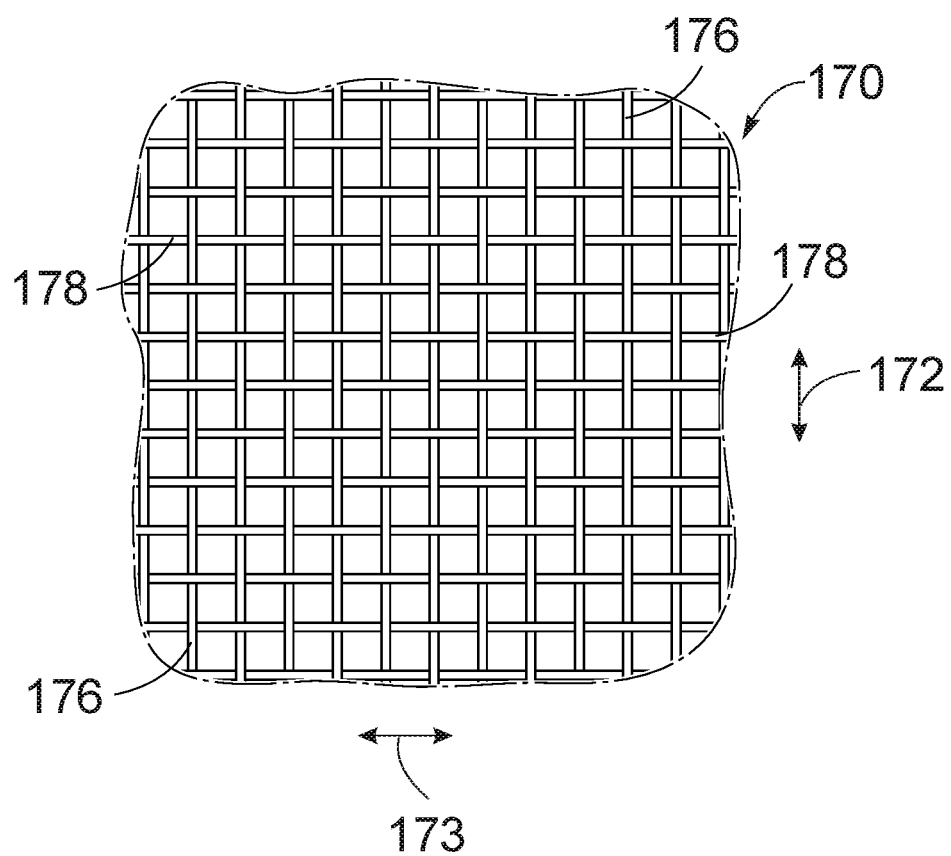
FIG. 44 shows a portion of an outer skirt fabric, detailing warp and weft fibers.

In some embodiments, the outer skirt 18 can comprise a fabric 170 that is stiffer in the axial direction 172 than it is in the circumferential direction 173 when mounted on frame 12 in order to enhance outward radial buckling or expansion of the outer skirt 18 (see FIG. 44). For example, the fabric 170 can be woven from a first set of fibers (or yarns or strands) 176, and a second set of fibers (or yarns or strands) 178. The fabric 170 can include a weave of warp fibers comprising the first set of fibers 176 and weft fibers comprising the second set of fibers 178. Alternatively, the fabric 170 can include a weave of warp fibers comprising the second set of fibers 178 and weft fibers comprising the first set of fibers 176.

The first set of fibers 176 can comprise monofilaments that are stiffer than the fibers in the second set of fibers 178. Examples of suitable monofilaments include, but are not limited to, those made of polymer or metal wires, such as PET, PTFE, and/or NiTi. In some embodiments, the monofilament can have a diameter of from about 0.05 mm to about 0.5 mm (about 0.002-0.02 inches). The second set of fibers 178 can comprise multifilaments and/or microfibers that are less stiff than the fibers in the first set of fibers 176. Examples of suitable multifilaments and/or microfibers include, but are not limited to, those made of polymer, such as PET and/or PTFE. In some embodiments, the second set of fibers 178 can comprise a mixture of materials (such as a mixture of multifilaments and microfibers) that has an overall stiffness that is less than the first set of fibers 176.

The fibers in the first or second sets of fibers do not need to be the same types of fibers, for example, the first set of fibers can include monofilaments, microfilaments, and/or microfibers, as long as the fabric 170 is stiffer in the axial direction than the circumferential direction when mounted on prosthetic valve 10. Likewise, the second set of fibers can include monofilaments, microfilaments, and/or microfibers.

In some embodiments, the fabric 170 comprises more parallel fibers per unit length in the axial direction than fibers per unit length in the circumferential direction. Thus, the fabric 170 includes an increased density of fibers running in the axial direction compared to fibers running in the circumferential direction.

Figure 57:
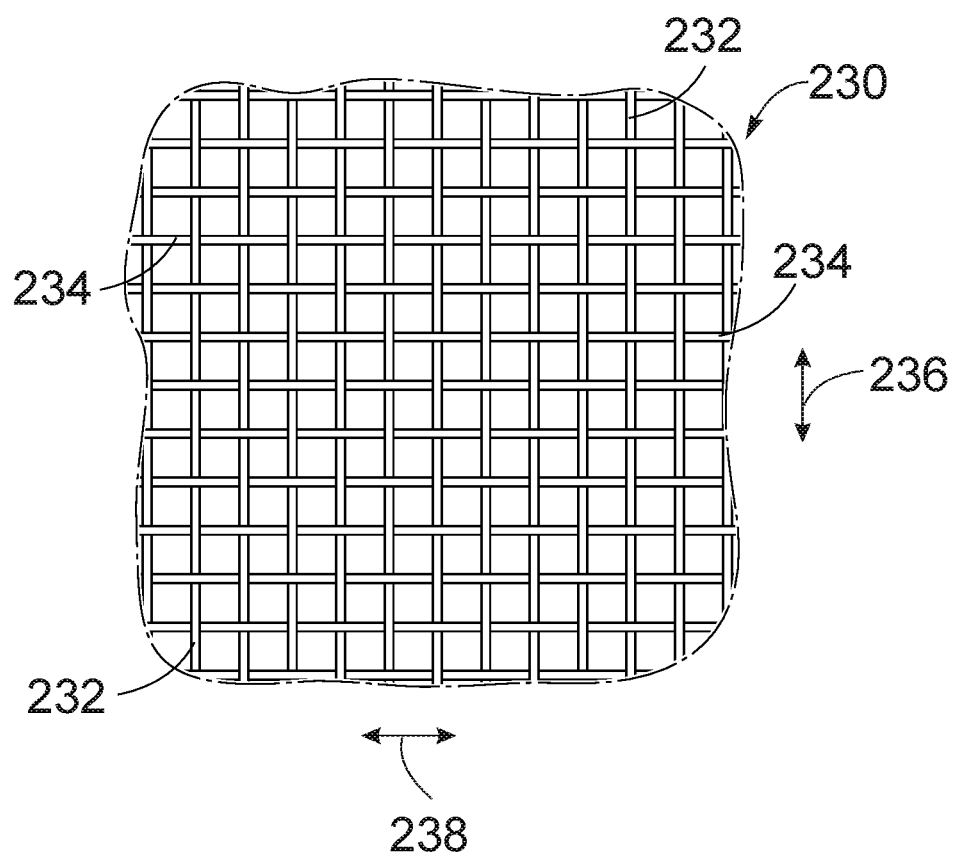
FIG. 57 shows a portion of an outer skirt fabric, detailing warp and weft fibers.

In additional embodiments, the outer skirt 18 can comprise a self-expandable fabric 230 that comprises one or more fibers made of a shape-memory material, such as NiTi (see FIG. 57). For example, the one or more fibers made of a shape-memory material can be included in the weave of the self-expandable fabric 230, or can be otherwise secured to attached (for example, by suture) to a fabric to make the self-expandable fabric 230. The shape memory of such fibers can be set to enhance the radial outward buckling or expansion of the outer skirt 18 when it is mounted on the frame 12. Additionally, the fibers of shape memory material in the self-expandable fabric 230 can be comprise different shape memories as needed to conform to particular anatomical structures. Thus, the self-expandable fabric 230 can be woven or constructed to have a plurality of fibers made of shape memory material with a shape memory set such that the fabric comprises a three-dimensional shape that conforms to particular anatomical structure in a patient.

When constructed of the self-expandable fabric 230, the outer skirt can be crimped to a radially collapsed configuration and restrained in the collapsed configuration by insertion of the prosthetic valve including the outer skirt into a sheath or equivalent mechanism of a delivery catheter. Once inside the body, the prosthetic valve can be advanced from the delivery sheath, which allows the prosthetic valve and the outer skirt to expand to their functional size.

With reference to FIG. 57, the self-expandable fabric 230 can be woven from a first set of fibers (or yarns or strands) 232, and a second set of fibers (or yarns or strands) 234. The self-expanding fabric 230 can be positioned on the frame 12 in any orientation that facilitates the radial outward buckling or expansion of the outer skirt 18. For example, as shown in FIG. 57, the self-expandable fabric 230 of the outer skirt 18 can include a weave of warp fibers in an axial direction 236 comprising the first set of fibers 232 and weft fibers in a circumferential direction 238 comprising the second set of fibers 234. In another embodiment, the self-expandable fabric 230 of the outer skirt 18 can include a weave of weft fibers in the axial direction 236 comprising the first set of fibers 232 and warp fibers in the circumferential direction 238 comprising the second set of fibers 234.

The first set of fibers 232 comprises one or more fibers that are made of a shape-memory material comprising a shape memory set to enhance the radially outward buckling of the outer skirt 18. For example, the fibers can be NiTi wires that have sufficient elongation to withstand weaving stress and a sufficiently large diameter to self-load and push adjacent fibers towards the set shape of the nitinol wire.

In several embodiments, such NiTi wires can comprise a diameter of from 0.5-15 Mils, such as from 4-6 Mils, from 1-5 Mils, from 2-5 Mils, from 3-5 Mils, from 4-7 Mils, or from 4-6 Mils in diameter. For example, in some embodiments, the NiTi wires can comprise a diameter of from 0.002 to 0.005 inches, such as about 0.002, about 0.003, about 0.004, or about 0.005 inches in diameter. The shape memory of any NiTi wires in the self-expandable fabric 230 can be set to a shape that will enhance the radial outward buckling of the outer skirt 18 before being woven into the fabric. In one example, the shape memory of the NiTi wires can be trained by heating to greater than 500° C. for 2 hours followed by aging at 450° C. for 90 minutes. The heating can be performed in an air or vacuum furnace followed by rapid (preferably water) quenching. After the shape memory of the NiTi wire is set, the wire can be woven into the self-expandable fabric 230. In some embodiments, 5-25 percent (such as 5-10, 5-15, 5-20, 10-15, 10-20, 10-25, 15-20, 15-25, or 20-25 percent) of the weft fibers in the self-expandable fabric of the outer skirt 18 can be made of the shape-memory material. In some embodiments, up to 100% of the weft fibers in the self-expandable fabric of the outer skirt 18 can be made of the shape-memory material.

In certain embodiments, the first set of fibers 232 (including the NiTi wires) are the weft fibers of the weave. In alternative embodiments, the first set of fibers 232 (including the NiTi wires) are the warp fibers of the weave. The remaining fibers in the first and second sets of fibers can also be made of a shape memory material (such as NiTi) comprising a shape memory set to enhance the radially outward buckling of outer skirt 18. Alternatively, the remaining fibers can be made of a non-shape-memory material, such as PET or PTFE. The remaining fibers do not need to be the same types of fibers, for example, the first and/or second set of fibers can include monofilaments, microfilaments, and/or microfibers. Examples of suitable monofilaments, microfilaments, and/or microfibers include, but are not limited to, those made of polymer such as PET or PTFE. In some embodiments, the monofilament or microfiber can have a diameter of from about 0.05 mm to about 0.5 mm (about 0.002-0.02 inches).

As noted above, the fabric 230 can be positioned on the frame 12 in any orientation that facilitates outward buckling and expansion of the outer skirt. In some implementations, the outer skirt 18 has shape memory fibers (e.g., NiTi wires) only in the axial direction. In other implementations, the outer skirt 18 has shape memory fibers (e.g., NiTi wires) only in the circumferential direction. In still other implementations, the outer skirt 18 has shape memory fibers (e.g., NiTi wires) in the axial and circumferential directions.

As shown in FIG. 57, the warp and weft fibers in the self-expandable fabric 230 can be in a plain weave. Alternative weave patterns can also be utilized. For example, the self-expandable fabric 230 can comprise a hybrid weave of non-shape memory warp and weft fibers (such as PET fibers) in a plain weave pattern alternating with shape-memory weft fibers and non-shape-memory warp fibers, or shape-memory warp fibers and non-shape-memory weft fibers, in a satin weave pattern (see FIGS. 58-60). In a satin weave pattern, the float length of the weft fibers is longer than in a plain weave pattern. Thus, when the shape memory fibers are used as weft fibers in a satin weave pattern, the outward buckling of the fabric can be increased due to fewer contact points which provides more freedom to the shape memory fibers to buckle outwards. Accordingly, the combination of the plain weave of non-shape-memory fibers with the satin weave of shape-memory and non-shape memory fibers provides an outer skirt material with superior radial outward buckling force.

Figure 58:
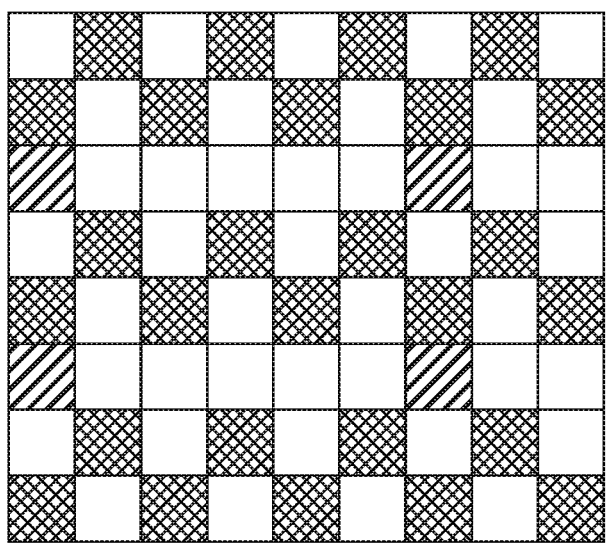
FIGS. 58-60 show a set of diagrams illustrating a portion of an outer skirt fabric, detailing the design of three different patterns of warp and weft fibers.
Figure 59:
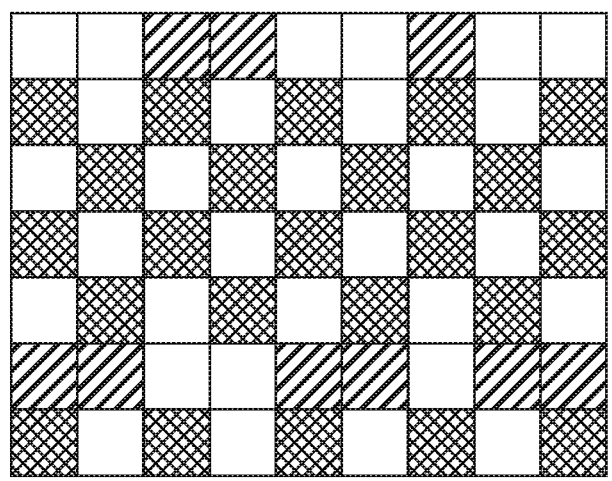
Figure 60:
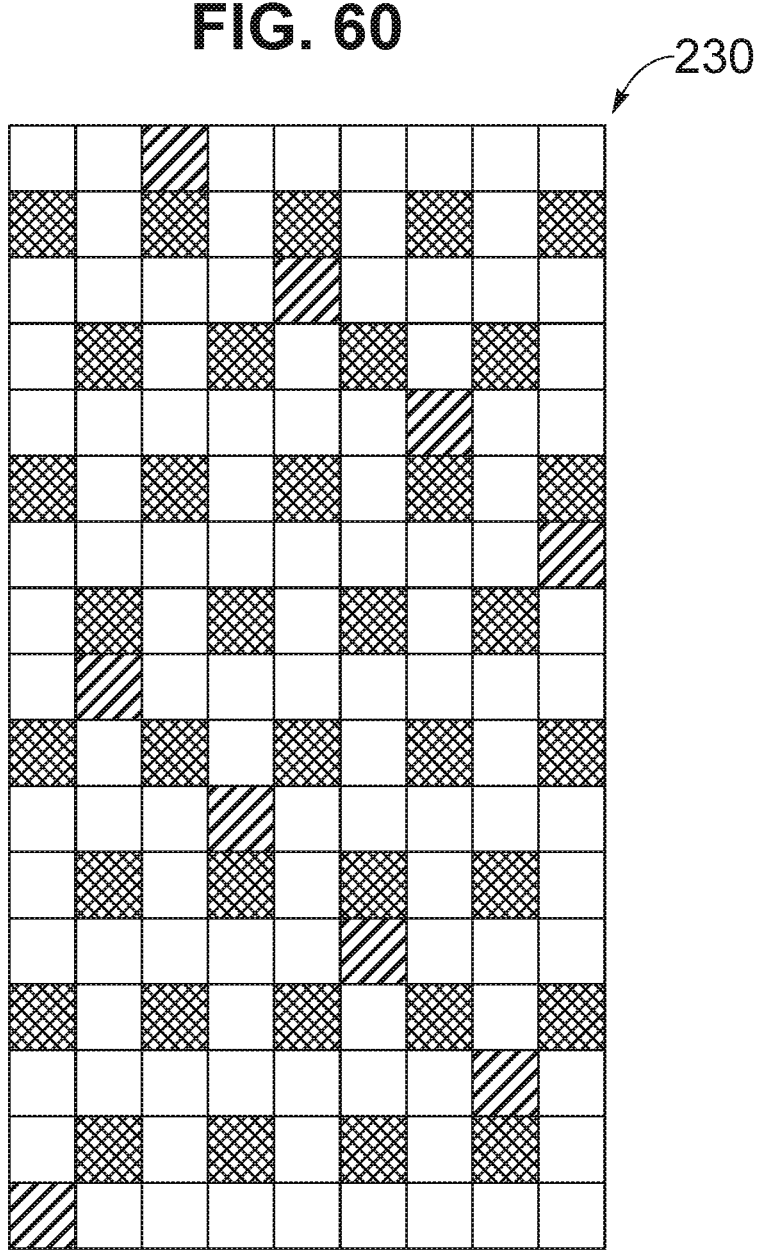

FIGS. 58-60 show weaving diagrams illustrating three exemplary designs for the weave of the self-expandable fabric 230. In the weaving diagrams shown in FIGS. 58-60, warp fibers are represented by columns and weft fibers are represented by rows. A square in the diagram represents the intersection of a warp fiber and a weft fiber. If the weft fiber is radially outward of the warp fiber at a particular intersection, then the square is marked with diagonal hatch (for shape memory fibers) or cross hatch (for non-shape memory fibers). If the warp fiber is radially outward of the weft fiber (that is, the warp fiber "floats" over the weft fiber) at a particular intersection, then the square is left blank. In the illustrated weaving diagrams, the weft fibers include the shape memory fibers. However, in other embodiments, the fibers can be reversed such that the weft fibers are the warp fibers and the warp fibers are the weft fibers and still provide the same weave pattern.

As illustrated in FIGS. 58-60, the rows of weft fibers in the weave can alternate between shape-memory fibers and non-shape memory fibers in various patterns. For example, one or more rows of shape-memory weft fibers can be separated by one or more (such as 2, 3, 4, or 5, or more) rows of non-shape-memory fibers. Additionally, the number of adjacent warp fibers that "float" over the shape-memory fiber in a particular row can also vary, for example from 1-2 adjacent warp fibers (e.g., as shown in FIG. 59), or 1-5 adjacent warp fibers, to up to 10 adjacent warp fibers (such as 2 adjacent warp fibers, 3 adjacent warp fibers, 4 adjacent ward fibers, 5 adjacent warp fibers (as shown in FIG. 58), 6 adjacent warp fibers, 7 adjacent warp fibers, 8 adjacent warp fibers (as shown in FIG. 60), or 9 adjacent warp fibers).

In some embodiments, the outer skirt 18 can comprise a self-expandable fabric 230 comprising a combination of plain and satin weave patterns with two rows of a plain weave of non-shape memory warp and weft fibers alternating with one row of a satin weave of a shape memory weft fiber and non-shape memory warp fibers. The satin weave can comprise a float of five adjacent warp fibers between radial outward exposure of the shape memory weft fiber over a single warp fiber (see FIG. 58).

In some embodiments, the outer skirt 18 can comprise a self-expandable fabric 230 comprising a combination of plain and satin weave patterns with four rows of a plain weave of non-shape memory warp and weft fibers alternating with one row of a satin weave of a shape memory weft fiber and non-shape memory warp fibers. The satin weave can comprise a float of one to adjacent two warp fibers between radial outward exposure of the shape memory weft fiber over one to two adjacent warp fibers (see FIG. 59).

In some embodiments, the outer skirt 18 can comprise a self-expandable fabric 230 comprising a combination of plain and satin weave patterns with one row of a plain weave of non-shape memory warp and weft fibers alternating with one row of a satin weave of a shape memory weft fiber and non-shape memory warp fibers. The satin weave can comprise a float of eight warp fibers between radial outward exposure of the shape memory weft fiber over a single warp fiber (see FIG. 60).

As shown in FIG. 48, in the collapsed configuration, the excess material of the outer skirt 18 forms a plurality of folds 179 extending in the axial direction. In this configuration, the first set of fibers 176 or 232 can extend axially in a substantially straight, non-folded configuration, and the second set of fibers 178 or 234 include the plurality of folds 179. In several embodiments, the elastic range of the second set of fibers is not exceeded when the prosthetic valve 10 is in the collapsed configuration and the outer skirt 18 forms the plurality of folds 179. Thus, when the prosthetic valve 10 is radially expanded from the collapsed configuration, there is no residual strain in the second set of fibers (i.e., there are no wrinkles formed in the second set of fibers). In several embodiments, the second set of fibers 178 or 234 comprises a set of multifilaments and/or microfibers each having an individual diameter that is small enough such that the elastic range of the multifilaments and/or microfibers is not exceeded when the prosthetic valve 10 is in the collapsed configuration and the outer skirt 18 comprises the plurality of folds 179. In such embodiments, there is no residual strain on the second set of fibers 178 or 234 after the prosthetic valve 10 has been compressed to the collapsed configuration. Thus, in several embodiments, the second set of fibers 178 or 234 comprises or consists of fibers that are "wrinklefree," that is, the second set of fibers 178 or 234 does not exceed its elastic range and does not comprise residual strain (i.e., wrinkles) after the prosthetic valve 10 is compressed to its fully collapsed configuration and has formed the plurality of folds 179 in the outer skirt 18.

When the prosthetic valve 10 is deployed within the body, the excess material of an intermediate portion of the outer skirt 18 that buckles outwardly can fill in gaps between the frame 12 and the surrounding native annulus to assist in forming a good, fluid-tight seal between the prosthetic valve and the native annulus. The outer skirt 18 therefore cooperates with the inner skirt 16 to avoid perivalvular leakage after implantation of the prosthetic valve 10. In several embodiments, the prosthetic valve 10 comprising the outer skirt 18 that buckles outwardly can have reduced perivalvular leakage when implanted in a subject compared to a similar prosthetic valve that lacks the outer skirt 18.

FIG. 48 shows the prosthetic valve 10 of FIGS. 1-3 and 42-43 mounted on an elongated shaft 180 of a delivery apparatus, forming a delivery assembly for implanting the prosthetic valve 10 in a patient's body. The prosthetic valve 10 is mounted in a radially collapsed configuration for delivery into the body. The shaft 180 comprises an inflatable balloon 182 for expanding the prosthetic valve within the body, the crimped prosthetic valve 10 being positioned over the deflated balloon. The frame 12 of the prosthetic valve 10, when in the radially compressed, mounted configuration, can comprise an inflow end portion 174 (see FIG. 46) that has an outer diameter $D_2$ that is smaller than the outer diameter $D_1$ of the outflow end portion of the frame. The tapering of the frame can be at least partially due to the V-shaped leaflets 40, as the V-shaped leaflets have less leaflet material within the inflow end portion of the frame 12 compared to a more rounded, U-shaped leaflet. Due to the tapered shape of the frame 12 in the mounted configuration, even with the additional thickness of the outer skirt 18 positioned around the inflow end portion 174 of the frame 12, the overall outer diameter of the inflow end portion of the prosthetic valve 10 can be about equal to, or less than, the overall outer diameter of the outflow end portion of the prosthetic valve.

Furthermore, as shown in FIG. 48, the prosthetic valve 10 can comprise commissure portions of the leaflets extending radially outwardly through corresponding window frame portions 30 to locations outside of the frame and sutured to the side struts of the commissure window frame. To minimize the crimp profile of the prosthetic valve, the window frame portions 30 can be depressed radially inwardly relative to the surrounding portions of the frame, such as the frame portions extending between adjacent commissure windows, when the prosthetic valve is radially compressed to the collapsed configuration on the shaft. For example, the commissure windows 30 of the frame can be depressed inwardly a radial distance of between from about 0.2 mm to about 1.0 mm relative to the portions of the frame extending between adjacent commissure windows when the prosthetic valve is radially collapsed. In this way, the outer diameter of the outflow end portion the prosthetic valve comprising the commissure portions can be generally consistent, as opposed to the commissure portions jutting outwardly from the surrounding portions of the prosthetic valve, which could hinder delivery of the prosthetic valve into the body. Even with the radially depressed commissure window frames 30, the outer diameter of the inflow end of the frame can still be smaller than, or about equal to, the outer diameter of the outflow end of the frame when the prosthetic valve is radially collapsed on the shaft, allowing for a minimal maximum overall diameter of the prosthetic valve. By minimizing the diameter of the prosthetic valve when mounted on the delivery shaft, the assembly can contained within a smaller diameter catheter and thus can be passed through smaller vessels in the body and can be less invasive in general.

Figure 49:
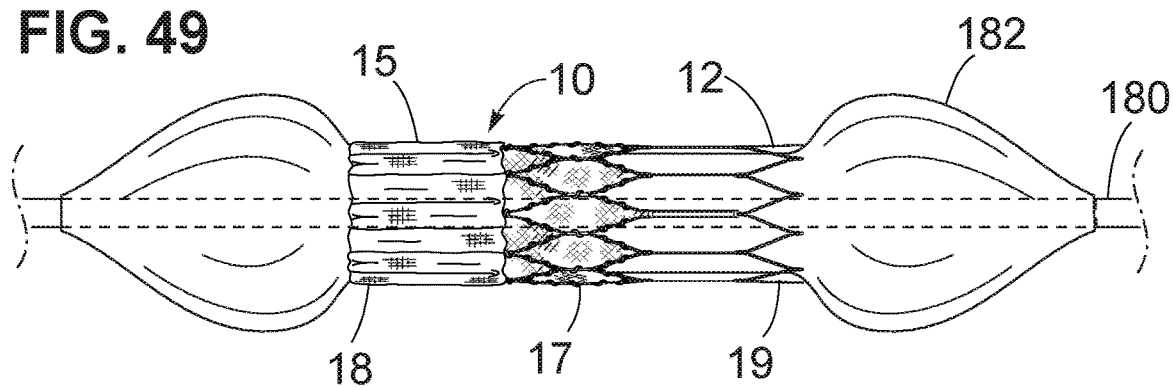
FIGS. 49-51 show balloon expansion of an alternative embodiment of a frame for a prosthetic valve having inflow and outflow end portions of reduced thickness.
Figure 50:
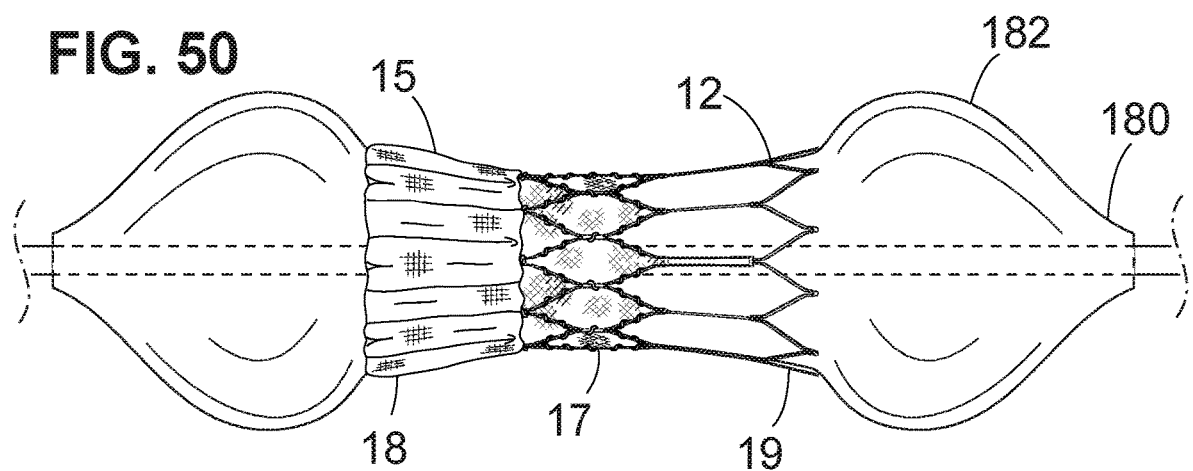
Figure 51:
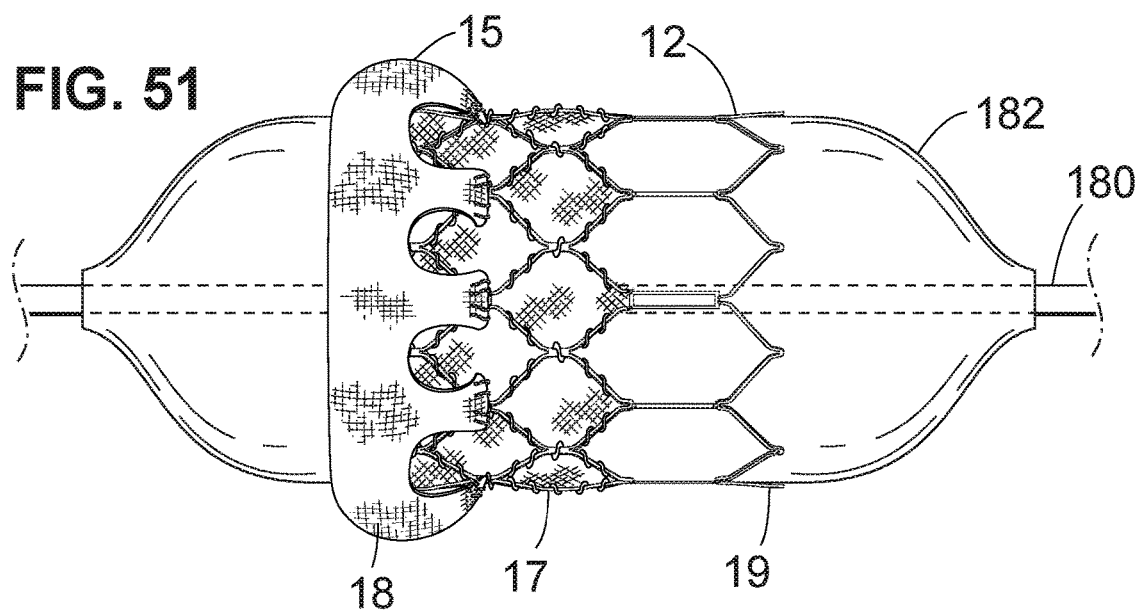

FIGS. 49-51 illustrate expansion of an embodiment of the prosthetic valve 10 from a radially collapsed configuration as shown in FIG. 49 to a radially expanded state as shown in FIG. 51. The prosthetic valve 10 is mounted on a balloon 182 of a delivery shaft 180, and comprises the inflow end portion 15, the outflow end portion 19 and the intermediate portion 17. For clarity, the outer skirt 18 and frame 12 of the prosthetic valve 10 is shown, but other components of the prosthetic valve, such as the leaflets and the inner skirt, are not shown. The frame 12 can have a reduced thickness at the inflow end portion 15 and at the outflow end portion 19, relative to the thickness of the intermediate portion 17. Due to the thinner end portions, when the balloon 182 is inflated the end portions 15 and 19 offer less resistance to expansion and expand faster than the intermediate portion 17, as shown in FIG. 50. Because the end portions expand faster than the intermediate portion, the frame 12 becomes confined on the balloon 182, inhibiting the frame from sliding towards either end of the balloon and reducing the risk of the frame sliding off the balloon prematurely. As shown in FIG. 51, further inflation of the balloon can cause the intermediate portion 17 of the frame to expand to the same final diameter as the end portions 15 and 19 for implantation, after which the balloon can be deflated and removed. Controlling the position of the prosthetic valve on the balloon can be important during delivery, especially with frames that foreshorten during expansion and move relative to the balloon. In the embodiment shown in FIGS. 49-51, the intermediate portion 17 of the frame can be held constant relative to the balloon while the two end portions foreshorten towards the intermediate portion due to the "dog-bone" effect of the balloon. Any suitable means can be used to produce the frame 12 with reduced thickness at the end portions 15 and 19, such as contacting the end portions with abrasive, drawing portions of a hypotube prior to laser cutting, laser ablation, water-jet machining, machining, or the like. In one embodiment, the end portions 15 and 19 of the frame have a thickness of about 0.37 mm while the intermediate portion 17 has a thickness of about 0.45 mm.

Although described in the context of prosthetic valve 10, the outer skirt 18 comprising the fabric 170 that is stiffer in the axial direction than in the circumferential direction, or the self-expandable fabric 230 comprising fibers made of shape memory material can be included as an outer skirt on any suitable prosthetic valve, such as any suitable prosthetic heart valve, known in the art. In several embodiments, the outer skirt 18 comprising the fabric 170 that is stiffer in the axial direction than in the circumferential direction or the self-expandable fabric 230 comprising fibers made of shape memory material can be included in place of an outer skirt on a known prosthetic heart valve. Non-limiting examples of suitable prosthetic heart valves for which that outer skirt 18 comprising the fabric 170 that is stiffer in the axial direction than the circumferential direction or the self-expandable fabric 230 comprising fibers made of shape memory material include those disclosed in U.S. and International Patent Publication Nos. US2012/0123529, WO2011/126758, WO2012/048035, WO2014/004822, WO2010/022138A2, U.S. Pat. Nos. 8,591,570, and 8,613,765, each of which is incorporated by reference herein in its entirety.

Further, although described in the context of the outer skirt 18 of the prosthetic valve 10, the self-expandable fabric 230 comprising fibers made of shape memory material can also be used in sheet form as a scaffold for tissue engineering with shape memory effect customized to particular anatomical shapes.

The prosthetic valve 10 can be configured for and mounted on a suitable delivery apparatus for implantation in a subject. Several catheter-based delivery apparatuses are known; a non-limiting example of a suitable catheter-based delivery apparatus includes that disclosed in U.S. Patent Application Publication Nos. US2012/0123529 and US2013/0030519, which are incorporated by reference herein in its entirety.

The prosthetic valve, once assembled, can be treated with any one of a combination of various chemical agents that can help to prevent rejection of the prosthetic valve by the recipient, to sterilize the prosthetic valve, to stabilize proteins in the prosthetic valve leaflet tissue, to make the tissue more resistant to mechanical fatigue, to reduce degradation of the tissue by proteolytic enzymes, and/or to allow packaging or delivery of the prosthetic valve in a dry form. In alternative embodiments, the leaflets of the prosthetic valve can be treated with chemical agents prior to being secured to the frame.

Some prosthetic heart valves are typically packaged in jars filled with preserving solution for shipping and storage prior to implantation into a patient, though techniques are also known for drying and storing bioprosthetic heart valves without immersing them in a preservative solution. The term "dried" or "dry" bioprosthetic heart valves refers simply to the ability to store those bioprosthetic heart valves without the preservative solutions, and the term "dry" should not be considered synonymous with brittle or rigid. Indeed, "dry" bioprosthetic heart valve leaflets may be relatively supple even prior to implant. There are a number of proposed methods for drying bioprosthetic heart valves, and for drying tissue implants in general, and the present application contemplates the use of bioprosthetic heart valves processed by any of these methods. A particularly preferred method of drying bioprosthetic heart valves is disclosed in U.S. Pat. No. 8,007,992 to Tian, et al. An alternative drying method is disclosed in U.S. Pat. No. 6,534,004 to Chen, et al. Again, these and other methods for drying bioprosthetic heart valves may be used prior to using the crimping systems and methods described herein.

One such strategy is to dehydrate the bioprosthetic tissue in a glycerol/ethanol mixture, to sterilize with ethylene oxide, and to package the final product "dry." This process eliminates the potential toxicity and calcification effects of glutaraldehyde as a sterilant and storage solution. There have been several methods proposed that use sugar alcohols (e.g., glycerol), alcohols, and combinations thereof in post-glutaraldehyde processing methods so that the resulting tissue is in a "dry" state rather than a wet state in which the tissue is stored in a solution comprising excess glutaraldehyde. U.S. Pat. No. 6,534,004 (Chen et al.) describes the storage of bioprosthetic tissue in polyhydric alcohols such as glycerol. In processes where the tissue is dehydrated in an ethanol/glycerol solution, the tissue may be sterilized using ethylene oxide (ETO), gamma irradiation, or electron beam irradiation.

More recently, Dove, et al. in U.S. Patent Application Publication No. 2009/0164005 propose solutions for certain detrimental changes within dehydrated tissue that can occur as a result of oxidation. Dove, et al. propose permanent capping of the aldehyde groups in the tissue (e.g., by reductive amination). Dove, et al. also describe the addition of chemicals (e.g., antioxidants) to the dehydration solution (e.g., ethanol/glycerol) to prevent oxidation of the tissue during sterilization (e.g., ethylene oxide, gamma irradiation, electron beam irradiation, etc.) and storage. Tissue processed in accordance with the principles disclosed in Dove, et al. are termed, "capped tissue", and therefore bioprosthetic heart valves which use such tissue are termed, "capped tissue valves". Capping the glutaraldehyde terminates the cross-linking process by consuming all or nearly all of the free aldehyde groups, and it is believed that this in conjunction with removing the prosthetic tissue valve from the cross-linking solution (e.g., glutaraldehyde) by storing dry is the most effective way to terminate the cross-linking process.

Once treated with appropriate chemical agents, the prosthetic valve can be crimped to a small profile, suited for implantation in a recipient and/or delivery to a health care provider. The prosthetic valve can be crimped directly onto a delivery device (e.g., on the balloon of a balloon catheter or on a shaft of a balloon catheter adjacent to the balloon). Once crimped, the prosthetic valve can be packaged in a sterile package in a dry state along with the delivery catheter (or just portion of the delivery catheter) on which the prosthetic valve is mounted and then delivered to a healthcare facility. The prosthetic valve and the delivery catheter can be stored until it is needed for a procedure, at which point the physician can remove the prosthetic valve and the delivery catheter from the package and then implant the prosthetic valve in a patient.

Figure 52:
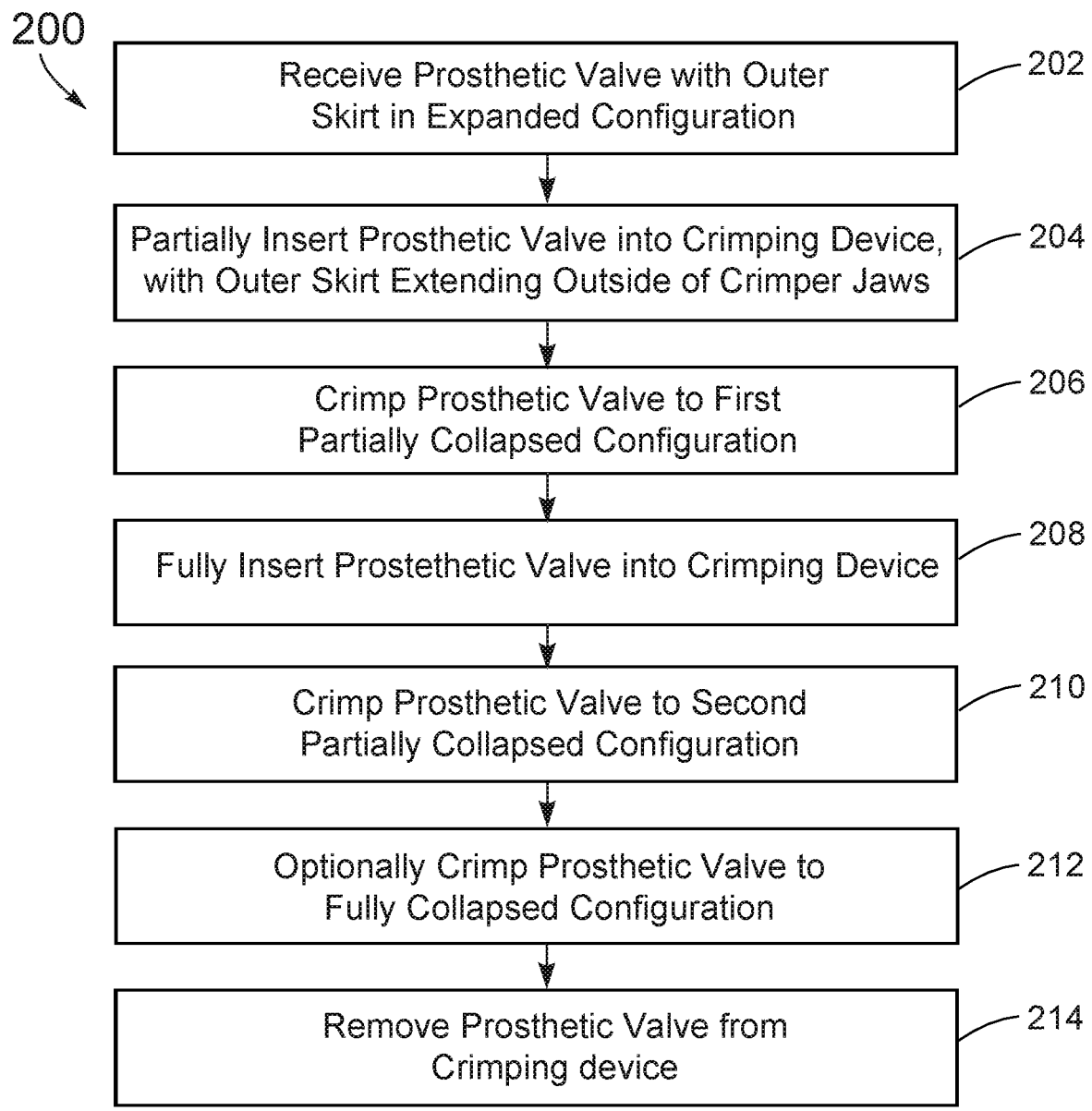
FIG. 52 illustrates a process for crimping an expandable and collapsible prosthetic valve including an outer skirt.

FIG. 52 illustrates a multi-step process 200 for crimping an expandable and collapsible prosthetic valve (such as a valve 12) comprising an outflow end portion and an inflow end portion, and an outer skirt (such as an outer skirt 18) on the inflow end portion. The outer skirt has an upper edge and a lower edge that are connected to the prosthetic valve, as described for outer skirt 18 above. By using the multi-step process 200, the prosthetic valve including an outer skirt (such as outer skirt 18) can be crimped to a small diameter without uneven buckling or crushing of the outer skirt. Using the multi-step process 200, the prosthetic valve can be crimped to a small profile, suited for implantation in a recipient. Alternatively, the prosthetic valve can be crimped to partially collapsed profile for delivery to a health care provider for further crimping prior to implantation in a recipient. The prosthetic valve can be crimped directly onto a delivery device (e.g., onto the balloon of a balloon catheter or onto a shaft of a balloon catheter adjacent the balloon). Once crimped (partially or fully), the prosthetic valve can be packaged in a sterile package alone or along with the delivery catheter and then delivered to a health care provider. The prosthetic valve and the delivery catheter can be stored until needed for a procedure, at which point the physician can remove the prosthetic valve and the delivery catheter from the package and then implant the prosthetic valve in a patient. In alternative embodiments, the prosthetic valve can be provided to health care providers in a fully expanded state. Process 200 can be used by the end user to crimp the prosthetic valve on a delivery apparatus just prior to implantation.

As shown in FIG. 52 at process block 202, the process 200 begins by receiving an expandable prosthetic valve in a fully expanded configuration. The crimping process can continue by partially inserting the expanded prosthetic valve into a valve crimper, at process block 204. The outflow end portion of the prosthetic valve can be inserted into the crimping device in a position where the jaws of the crimping device can contact the frame of the prosthetic valve. The portion of the prosthetic valve covered with the outer skirt is located outside the crimping aperture of the crimping device such that the crimper jaws (when actuated) do not contact the outer skirt, or, alternatively, contact the upper edge or portion of the outer skirt (such as the upper edge of outer skirt 18 or the plurality of alternating projections 164 and notches 166 of outer skirt 18), but do not contact the intermediate portion of the outer skirt.

At process block 206, the prosthetic valve is crimped to a first partially collapsed configuration. As discussed above for outer skirt 18, when the collapsible and expandable prosthetic valve is crimped to the fully collapsed configuration, the distance between the upper and lower attachment point of the outer skirt elongates, resulting in flattening of the outer skirt against the frame of the prosthetic valve. Thus, when the prosthetic valve is crimped to the first partially collapsed configuration at process block 206, the distance between the upper and lower attachment point of the outer skirt elongates resulting in partial flattening of the outer skirt against the frame of the prosthetic valve. This partial flattening is due to the elongation for the frame of the prosthetic valve in the axial direction. Due to the partial flattening, axially extending folds form in the outer skirt. Although the prosthetic valve is not fully inserted into the crimper, radial compression of the portion of the prosthetic valve that is inserted between the crimper jaws results in a corresponding radial collapse of the portion of the prosthetic valve that is not inserted between the crimper jaws during this crimping step.

In some embodiments, an expandable prosthetic valve can be considered crimped to the first partially collapsed configuration and process block 206 can accordingly be considered complete when the distance between the upper and lower attachment point of the outer skirt is elongated to about 20%, about 30%, about 40%, about 50%, or about 60% (such as between about 20% and about 60%) of the distance between the upper and lower attachment point of the outer skirt in the fully collapsed configuration, resulting in partial flattening of the outer skirt against the frame of the prosthetic valve. In other embodiments, an expandable prosthetic valve can be considered crimped to the first partially collapsed configuration and process block 206 can accordingly be considered complete when the prosthetic valve has a diameter that is about 60% or about 50% (such as between about 40% and about 60%) of the diameter of the prosthetic valve in the fully expanded configuration. In more embodiments, an expandable prosthetic valve can be considered crimped to the first partially collapsed configuration and process block 206 can accordingly be considered complete when the valve outside diameter is be from about 15-20 mm at the outflow side, and from about 15-26 mm at the inflow side. The difference in outer diameter between the inflow and outflow sides of the valve is due to the outer skirt, which can add from about 1-5 mm to the outside diameter of the inflow end portion.

At process block 208, the prosthetic valve is fully inserted into the crimping jaws.

The crimping process can continue at process block 210 by crimping the expandable prosthetic valve to a second partially collapsed configuration. In some embodiments, the expandable prosthetic valve can be considered crimped to the second partially collapsed configuration and process block 210 can accordingly be considered complete when the distance between the upper and lower attachment point of the outer skirt is elongated to about 70%, about 80%, or about 90% (such as at least about 70%) of the distance between the upper and lower attachment points of the outer skirt in the fully collapsed configuration, resulting in additional flattening of the outer skirt against the frame of the prosthetic valve. In other embodiments, an expandable prosthetic valve can be considered crimped to the second partially collapsed configuration and process block 206 can accordingly be considered complete when the prosthetic valve has a diameter that is about 40% or about 30% (such as no more than about 40%) of the diameter of the prosthetic valve in the fully expanded configuration. The outer skirt can add from about 1-4 mm to the outside diameter of the inflow end portion of the valve in the second partially collapsed configuration.

The crimping process can optionally continue at process block 212 by crimping the expandable prosthetic valve to a fully collapsed configuration. In some embodiments, the expandable prosthetic valve can be considered crimped to the fully collapsed configuration and process block 212 can accordingly be considered complete when the diameter of the frame 12 of the prosthetic valve 10 is no more than about 5 mm. In additional embodiments the frame 12 of the prosthetic valve 10 has a diameter of no more than about 14 Fr in the fully crimped configuration. In one non-limiting example, the frame of a 26-mm prosthetic valve, when fully crimped, has a diameter of no more than about 14 Fr. The outer skirt can add about 1 Fr to the outside diameter of the inflow end portion of the valve in the fully collapsed configuration.

The crimping process can continue by removing the prosthetic valve from the crimping device at process block 214. At the completion of any of the process blocks 202, 204, 206, 208, and/or 210, the process can be paused for any appropriate period of time. That is, a succeeding process block need not begin immediately upon termination of a preceding process block.

In various embodiments, the prosthetic valve can be removed from the crimping device at the completion of steps 206 or 210 and then packaged in a sterile package for storage and/or delivery to a health care provider, with the remaining steps of the process 200 to be completed by the end user. In particular embodiments, the crimped or partially crimped prosthetic valve is packaged in a dry state. In alternative embodiments, the crimped or partially crimped prosthetic valve is packaged in a "wet" state within a container containing a preserving solution.

Figure 53:
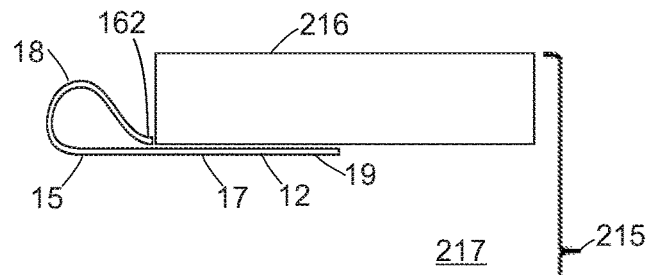
FIGS. 53-56 illustrate a process for crimping an expandable and collapsible prosthetic valve including an outer skirt.
Figure 54:
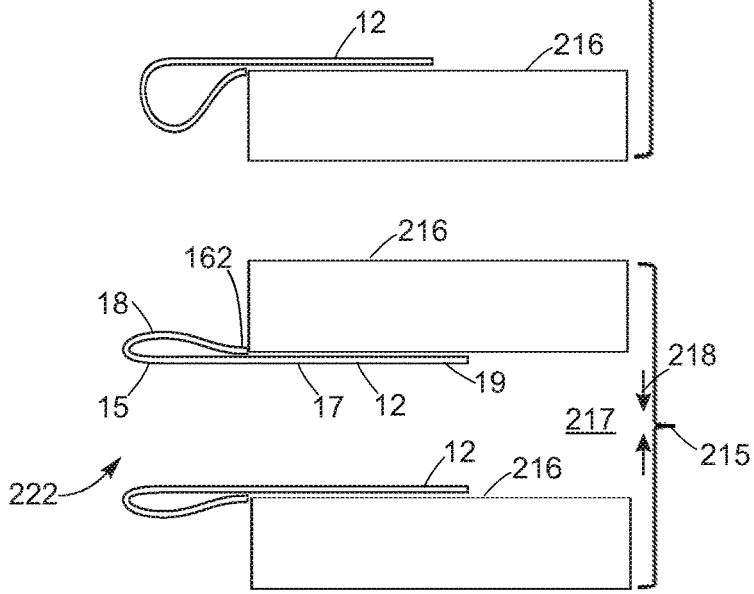
Figure 55:
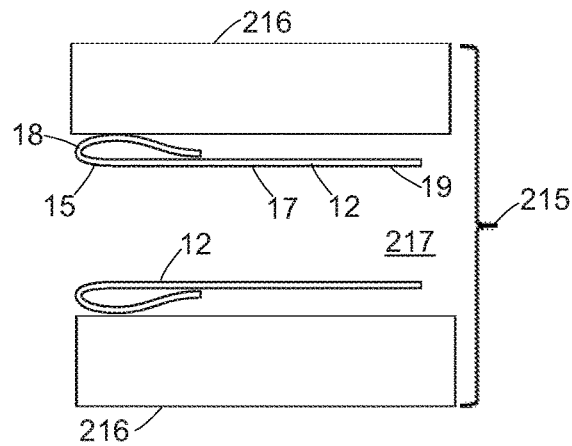

FIGS. 53-55 schematically illustrate process blocks 204-210 of the multi-step process 200 for crimping an expandable and collapsible prosthetic valve comprising an outer skirt, in the context of crimping the prosthetic valve 10 comprising the outer skirt 18 using a crimping device 215. The crimping device 215 can include a plurality of circumferentially arranged crimping jaws 216 (two of which are shown in the drawings) that define a variable diameter crimping aperture 217. The crimping jaws 216 can be moved radially inwardly relative to each other to decrease the size of the aperture 217, thereby radially compressing a prosthetic valve disposed in the aperture 217. Further details regarding the construction of the crimping device 215 are disclosed in U.S. Pat. No. 7,530,253, which is incorporated by reference herein in its entirety.

As shown in FIG. 53, the outflow end portion 19 of the prosthetic valve 10 in a fully expanded configuration can be inserted between the crimper jaws 216 of the crimping device 215 up to the upper edge 162 of the outer skirt 18. The inflow end portion 15 of the prosthetic valve 10 including the outer skirt 18 protrudes from the crimper jaws 216, such that the crimper jaws (when actuated to move radially inwardly) do not contact the outer skirt 18. In an alternative embodiment (not pictured), the prosthetic valve 10 can be inserted into the crimping device 215 up to the plurality of alternating notches 166 (FIG. 41), such that the crimper jaws 216 (when actuated) contact the plurality of alternating projections 164 and notches 166, but do not contact the remainder of the outer skirt 18.

As shown in FIG. 54, the crimper jaws are moved radially inwardly in the direction of arrows 218, resulting in radial compression of the prosthetic valve 10 to the first partially collapsed configuration 222. As the prosthetic valve 10 collapses, the distance between the upper and lower attachment point of the outer skirt 18 elongates, resulting in partial flattening of the outer skirt against the frame 12 of the prosthetic valve 10. Following crimping to the first partially collapsed configuration 222, the prosthetic valve 10 is fully inserted into the crimper jaws 216 of crimping device 215 (FIG. 55).

Figure 56:
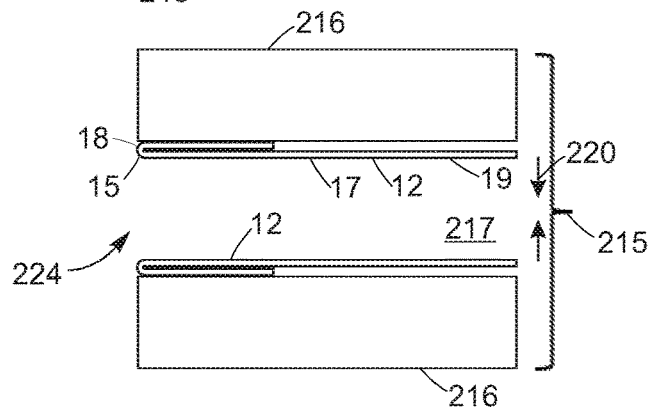

As shown in FIG. 56, the crimper jaws are moved further radially inwardly in the direction of arrows 220, resulting in radial compression of the prosthetic valve 10 to the second partially collapsed configuration 224. As the prosthetic valve 10 collapses, the distance between the upper and lower attachment point of the outer skirt 18 elongates, resulting in additional flattening of the outer skirt against the frame 12 of the prosthetic valve 10.

The prosthetic valve 10 can be removed from the crimping device following crimping to the second partially crimped configuration 224. For example, in some embodiments, the prosthetic valve 10 can be crimped to the second partially collapsed configuration and then removed from the crimping device and packaged for storage or delivery to a health care provider, and the prosthetic valve can be fully crimped by a physician before implantation into a subject. In other embodiments, the prosthetic valve 10 can be further crimped to a fully collapsed configuration before removal from the crimping device and then packaged for storage and/or delivery to the health care provider.

The rate at which the prosthetic valve is crimped can be adjusted as needed for particular valves and/or crimping devices. For example, the expandable prosthetic valve can be crimped to a first partially crimped configuration at a first rate, then crimped to a second partially crimped configuration at a second rate, then fully crimped at a third rate. In another alternative embodiment, the rate at which an expandable prosthetic valve is crimped can be continuously variable and determined based on suitable factors such as the pressure resulting in the leaflets from the crimping process.

The process 200 can be used with a wide variety of prosthetic valves that have an outer skirt, as well as with a wide variety of crimping devices. The process of crimping a prosthetic valve and controlling the speed at which a prosthetic valve is crimped can be controlled and completed by any of various crimping devices. For example, a prosthetic valve can be crimped manually using a manual crimping device (such as disclosed in U.S. Pat. No. 7,530, 253, incorporated by reference herein in its entirety), or automatically using an automated crimping device (such as disclosed in U.S. patent application Ser. No. 14/211,775, filed Mar. 14, 2014, which is incorporated by reference herein in its entirety). A prosthetic valve can also be partially crimped using a crimping device (such as an automatic or manual crimping device disclosed in U.S. Pat. No. 7,530, 253 or U.S. patent application Ser. No. 14/211,775) for the first and second crimping steps, and then removed from the crimping device and in a further crimping step pulled through a crimping cone into a delivery sheath or a cylinder, which has an inside diameter equal to the final crimped diameter of the prosthetic valve (such as described in U.S. Patent Application Publication No. 2012/0239142, which is incorporated by reference herein in its entirety).

Appropriate crimping devices can be driven by an electric motor or a combustion engine, can be pressure regulated, or can be pneumatically or hydraulically driven. Such a system can include various devices for collecting user input, such as buttons, levers, pedals, etc.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope of these claims.

We claim:

1. An implantable prosthetic valve comprising:
    an annular frame comprising an inflow end and an outflow end and being radially collapsible and expandable between a radially collapsed configuration and a radially expanded configuration, the frame defining an axial direction extending from the inflow end to the outflow end;
    a leaflet structure positioned within the frame and secured thereto; and
    an annular outer skirt positioned around an outer surface of the frame, wherein the outer skirt comprises:
        an inflow edge secured to the frame at a first location,
        an outflow edge secured to the frame at a second location;

an intermediate portion between the inflow edge and the outflow edge that comprises slack that buckles radially outwards from the inflow and outflow edges of the annular outer skirt when the valve is in the expanded configuration; and a self-expandable fabric comprising fibers extending in the axial direction of the valve and made of shape memory material having a shape memory set to enhance the radially outward buckling of the slack of the outer skirt.

2. The valve of claim 1, wherein the outflow edge of the outer skirt comprises a plurality of alternating projections and notches, the projections secured to the frame at the second location, the notches not directly secured to the frame.

3. The valve of claim 1, wherein when the frame is in the collapsed configuration, a distance in the axial direction between the inflow edge of the outer skirt and the outflow edge of the outer skirt is greater than when the valve is in the expanded configuration, reducing the slack in the intermediate portion between the inflow edge and the outflow edge of the outer skirt.

4. The valve of claim 1, wherein the self-expandable fabric comprises fibers that do not comprise residual strain after the frame is expanded to the expanded configuration from the collapsed configuration.

5. The valve of claim 1, wherein the self-expandable fabric comprises a weave of warp fibers and weft fibers.

6. The valve of claim 5, wherein the weave of warp fibers and weft fibers comprises:
   a plain weave pattern comprising fibers made of non-shape memory material; and
   a satin weave pattern comprising the fibers made of the shape memory material.

7. The valve claim 6, wherein the weave of warp fibers and weft fibers comprises two rows of a plain weave of non-shape memory warp and weft fibers alternating with one row of a satin weave of a shape memory weft fiber and non-shape memory warp fibers.

8. The valve of claim 6, wherein the weave of warp fibers and weft fibers comprises four rows of a plain weave of non-shape memory warp and weft fibers alternating with one row of a satin weave of a shape memory weft fiber and non-shape memory warp fibers.

9. The valve claim 6, wherein the satin weave comprises a float of five adjacent warp fibers between outwardly exposed weft fibers made of shape memory material.

10. The valve claim 6, wherein the satin weave comprises a float of eight adjacent warp fibers between outwardly exposed weft fibers made of shape memory material.

11. The valve of claim 5, wherein 5-25 percent of the weft fibers in the self-expandable fabric are made of the shape-memory material.

12. The valve claim 1, wherein the self-expandable fabric comprises a hybrid weave of non-shape-memory warp fibers and weft fibers in a plain weave pattern alternating with shape memory weft fibers and non-shape memory warp fibers in a satin weave pattern.

13. The valve of claim 1, wherein the shape-memory material is a nickel titanium alloy.

14. The valve of claim 1, wherein the fibers made of shape memory material comprise a diameter of from 0.5 to 15 Mils.

15. The valve of claim 1, wherein the annular frame comprises a plurality of leaflet attachment portions; and the leaflet structure is secured to the leaflet attachment portions of the frame.

16. The valve of claim 1, wherein the self-expandable fabric comprises a hybrid weave of non-shape memory fibers in a plain weave pattern alternating with shape memory axial fibers and non-shape memory circumferential fibers in a satin weave pattern.

17. An assembly for implanting a prosthetic heart valve in a patient's body comprising:
   a delivery apparatus comprising an elongated shaft; and
   the prosthetic valve of claim 1 mounted on the shaft in a radially collapsed configuration for delivery into the body.

18. An implantable prosthetic valve, comprising:
   an annular frame comprising an inflow end and an outflow end and being radially collapsible and expandable between a radially collapsed configuration and a radially expanded configuration, the frame defining an axial direction extending from the inflow end to the outflow end;
   a leaflet structure positioned within the frame and secured thereto; and
   an annular outer skirt positioned around an outer surface of the frame, wherein the outer skirt comprises:
      an inflow edge secured to the frame at a first location,
      an outflow edge secured to the frame at a second location;
      an intermediate portion between the inflow edge and the outflow edge that comprises slack that buckles radially outwards from the inflow and outflow edges of the annular outer skirt when the valve is in the expanded configuration; and
      a self-expandable fabric comprising fibers extending in the axial direction of the valve and made of shape memory material having a shape memory set to enhance the radially outward buckling of the slack of the outer skirt, wherein the self-expandable fabric comprises a weave of warp fibers and weft fibers and wherein 10-15 percent of the weft fibers in the self-expandable fabric are made of the shape-memory material.

19. An implantable prosthetic valve, comprising:
   an annular frame comprising an inflow end and an outflow end and being radially collapsible and expandable between a radially collapsed configuration and a radially expanded configuration, the frame defining an axial direction extending from the inflow end to the outflow end;
   a leaflet structure positioned within the frame and secured thereto; and
   an annular outer skirt positioned around an outer surface of the frame, wherein the outer skirt comprises:
      an inflow edge secured to the frame at a first location,
      an outflow edge secured to the frame at a second location;
      an intermediate portion between the inflow edge and the outflow edge that comprises slack that buckles radially outwards from the inflow and outflow edges of the annular outer skirt when the valve is in the expanded configuration; and
      a self-expandable fabric comprising fibers extending in the axial direction of the valve and made of shape memory material having a shape memory set to enhance the radially outward buckling of the slack of the outer skirt, wherein the fibers made of shape memory material comprise a diameter of from 4-6 Mils.

\* \* \* \* \*